United States Patent
Agrawal et al.

(10) Patent No.: US 8,886,125 B2
(45) Date of Patent: *Nov. 11, 2014

(54) DISTANCE-BASED ASSOCIATION

(75) Inventors: Avneesh Agrawal, San Diego, CA (US);
Chong U. Lee, San Diego, CA (US);
Kamran Moallemi, Del Mar, CA (US);
David Jonathan Julian, San Diego, CA (US); Manuel E. Jaime, Solana Beach, CA (US); Robert Keith Douglas, San Diego, CA (US); Gregory Gordon Rose, San Diego, CA (US); Lu Xiao, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 932 days.

This patent is subject to a terminal disclaimer.

(21) Appl. No.: 11/692,100

(22) Filed: Mar. 27, 2007

(65) Prior Publication Data

US 2007/0287386 A1  Dec. 13, 2007

Related U.S. Application Data

(60) Provisional application No. 60/792,035, filed on Apr. 14, 2006.

(51) Int. Cl.
| | |
|---|---|
| *H04B 7/00* | (2006.01) |
| *G01S 13/76* | (2006.01) |
| *H04L 29/08* | (2006.01) |
| *G01S 13/28* | (2006.01) |
| *G01S 13/02* | (2006.01) |
| *H04W 4/02* | (2009.01) |
| *H04W 8/00* | (2009.01) |
| *H04W 4/00* | (2009.01) |

(52) U.S. Cl.
CPC ............. *G01S 13/765* (2013.01); *G01S 13/284* (2013.01); *G01S 13/0209* (2013.01); *H04W 4/027* (2013.01); *H04W 4/02* (2013.01); *H04L 67/24* (2013.01); *H04W 4/023* (2013.01); *H04W 8/005* (2013.01); *H04W 4/001* (2013.01)

USPC .......................... 455/41.3; 455/41.2; 455/41.1

(58) Field of Classification Search
CPC ...... H04W 84/18; H04W 88/06; H04W 76/02
USPC ................. 455/41.2, 414.1, 404.2, 41.1, 41.3
See application file for complete search history.

(56) References Cited

U.S. PATENT DOCUMENTS

| 4,006,477 A | 2/1977 | Yost, Jr. et al. |
| 5,382,957 A | 1/1995 | Blume |

(Continued)

FOREIGN PATENT DOCUMENTS

| CN | 1432949 A | 7/2003 |
| CN | 1633660 A | 6/2005 |

(Continued)

OTHER PUBLICATIONS

International Search Report—PCT/US07/066731—International Search Authority—European Patent Office—Nov. 9, 2007.

(Continued)

*Primary Examiner* — Nay A Maung
*Assistant Examiner* — Angelica M Perez
(74) *Attorney, Agent, or Firm* — Paul S. Holdaway

(57) ABSTRACT

Various operations may be performed based on a distance-related function associated with two or more devices. For example, an association procedure for two or more devices may be based on one or more determined distances. Similarly, presence management may be based on one or more determined distances. A distance-related function may take various form including, for example, a distance between devices, two or more distances between devices, a rate of change in a relative distance between devices, relative acceleration between devices, or some combination of two or more of the these distance-related functions.

88 Claims, 7 Drawing Sheets

(56) References Cited

U.S. PATENT DOCUMENTS

| | | |
|---|---|---|
| 5,687,169 A | 11/1997 | Fullerton |
| 5,764,696 A | 6/1998 | Barnes et al. |
| 5,812,081 A | 9/1998 | Fullerton |
| 5,832,035 A | 11/1998 | Fullerton |
| 5,907,427 A | 5/1999 | Scalora et al. |
| 5,952,956 A | 9/1999 | Fullerton |
| 5,960,031 A | 9/1999 | Fullerton et al. |
| 5,963,581 A | 10/1999 | Fullerton et al. |
| 5,969,663 A | 10/1999 | Fullerton et al. |
| 5,970,148 A | 10/1999 | Meier |
| 5,995,534 A | 11/1999 | Fullerton et al. |
| 6,025,795 A | 2/2000 | Hulderman et al. |
| 6,031,862 A | 2/2000 | Fullerton et al. |
| 6,091,374 A | 7/2000 | Barnes |
| 6,111,536 A | 8/2000 | Richards et al. |
| 6,133,876 A | 10/2000 | Fullerton et al. |
| 6,177,903 B1 | 1/2001 | Fullerton et al. |
| 6,218,979 B1 | 4/2001 | Barnes et al. |
| 6,295,019 B1 | 9/2001 | Richards et al. |
| 6,297,773 B1 | 10/2001 | Fullerton et al. |
| 6,300,903 B1 | 10/2001 | Richards et al. |
| 6,304,623 B1 | 10/2001 | Richards et al. |
| 6,332,193 B1 | 12/2001 | Glass et al. |
| 6,351,652 B1 | 2/2002 | Finn et al. |
| 6,354,946 B1 | 3/2002 | Finn |
| 6,400,307 B2 | 6/2002 | Fullerton et al. |
| 6,400,329 B1 | 6/2002 | Barnes |
| 6,421,389 B1 | 7/2002 | Jett et al. |
| 6,430,208 B1 | 8/2002 | Fullerton et al. |
| 6,437,756 B1 | 8/2002 | Schantz |
| 6,462,701 B1 | 10/2002 | Finn |
| 6,466,125 B1 | 10/2002 | Richards et al. |
| 6,469,628 B1 | 10/2002 | Richards et al. |
| 6,483,461 B1 | 11/2002 | Matheney et al. |
| 6,489,893 B1 | 12/2002 | Richards et al. |
| 6,492,904 B2 | 12/2002 | Richards |
| 6,492,906 B1 | 12/2002 | Richards et al. |
| 6,501,393 B1 | 12/2002 | Richards et al. |
| 6,504,483 B1 | 1/2003 | Richards et al. |
| 6,512,455 B2 | 1/2003 | Finn et al. |
| 6,512,488 B2 | 1/2003 | Schantz |
| 6,519,464 B1 | 2/2003 | Santhoff et al. |
| 6,529,568 B1 | 3/2003 | Richards et al. |
| 6,538,615 B1 | 3/2003 | Schantz |
| 6,539,213 B1 | 3/2003 | Richards et al. |
| 6,549,567 B1 | 4/2003 | Fullerton |
| 6,552,677 B2 | 4/2003 | Barnes et al. |
| 6,556,621 B1 | 4/2003 | Richards et al. |
| 6,560,463 B1 | 5/2003 | Santhoff |
| 6,571,089 B1 | 5/2003 | Richards et al. |
| 6,573,857 B2 | 6/2003 | Fullerton et al. |
| 6,577,691 B2 | 6/2003 | Richards et al. |
| 6,585,597 B2 | 7/2003 | Finn |
| 6,593,886 B2 | 7/2003 | Schantz |
| 6,606,051 B1 | 8/2003 | Fullerton et al. |
| 6,611,234 B2 | 8/2003 | Fullerton et al. |
| 6,611,811 B1 | 8/2003 | Deaton et al. |
| 6,614,384 B2 | 9/2003 | Hall et al. |
| 6,614,387 B1 | 9/2003 | Deadman |
| 6,621,462 B2 | 9/2003 | Barnes |
| 6,636,566 B1 | 10/2003 | Roberts et al. |
| 6,636,567 B1 | 10/2003 | Roberts et al. |
| 6,636,573 B2 | 10/2003 | Richards et al. |
| 6,642,903 B2 | 11/2003 | Schantz |
| 6,650,894 B1 | 11/2003 | Berstis et al. |
| 6,661,342 B2 | 12/2003 | Hall et al. |
| 6,667,724 B2 | 12/2003 | Barnes et al. |
| 6,670,909 B2 | 12/2003 | Kim |
| 6,671,310 B1 | 12/2003 | Richards et al. |
| 6,674,396 B2 | 1/2004 | Richards et al. |
| 6,677,796 B2 | 1/2004 | Brethour et al. |
| 6,700,538 B1 | 3/2004 | Richards |
| 6,710,736 B2 | 3/2004 | Fullerton et al. |
| 6,717,992 B2 | 4/2004 | Cowie et al. |
| 6,748,040 B1 | 6/2004 | Johnson et al. |
| 6,750,757 B1 | 6/2004 | Gabig, Jr. et al. |
| 6,759,948 B2 | 7/2004 | Grisham et al. |
| 6,760,387 B2 | 7/2004 | Langford et al. |
| 6,762,712 B2 | 7/2004 | Kim |
| 6,763,057 B1 | 7/2004 | Fullerton et al. |
| 6,763,282 B2 | 7/2004 | Glenn et al. |
| 6,774,764 B2 | 8/2004 | Ghosh et al. |
| 6,774,846 B2 | 8/2004 | Fullerton et al. |
| 6,774,859 B2 | 8/2004 | Schantz et al. |
| 6,778,603 B1 | 8/2004 | Fullerton et al. |
| 6,781,530 B2 | 8/2004 | Moore |
| 6,782,048 B2 | 8/2004 | Santhoff |
| 6,788,730 B1 | 9/2004 | Richards et al. |
| 6,822,604 B2 | 11/2004 | Hall et al. |
| 6,823,022 B1 | 11/2004 | Fullerton et al. |
| 6,836,223 B2 | 12/2004 | Moore |
| 6,836,226 B2 | 12/2004 | Moore |
| 6,844,816 B1 | 1/2005 | Melton et al. |
| 6,845,253 B1 | 1/2005 | Schantz |
| 6,847,675 B2 | 1/2005 | Fullerton et al. |
| 6,862,575 B1 | 3/2005 | Anttila et al. |
| 6,879,878 B2 | 4/2005 | Glenn et al. |
| 6,882,301 B2 | 4/2005 | Fullerton |
| 6,895,034 B2 | 5/2005 | Nunally et al. |
| 6,895,236 B2 | 5/2005 | Shuster |
| 6,898,434 B2 | 5/2005 | Pradhan et al. |
| 6,900,732 B2 | 5/2005 | Richards |
| 6,906,625 B1 | 6/2005 | Taylor et al. |
| 6,907,244 B2 | 6/2005 | Santhoff et al. |
| 6,907,270 B1 | 6/2005 | Blanz |
| 6,912,240 B2 | 6/2005 | Kumar et al. |
| 6,914,949 B2 | 7/2005 | Richards et al. |
| 6,917,284 B2 | 7/2005 | Grisham et al. |
| 6,919,838 B2 | 7/2005 | Santhoff |
| 6,922,166 B2 | 7/2005 | Richards et al. |
| 6,922,177 B2 | 7/2005 | Barnes et al. |
| 6,925,109 B2 | 8/2005 | Richards et al. |
| 6,933,882 B2 | 8/2005 | Fullerton |
| 6,937,639 B2 | 8/2005 | Pendergrass et al. |
| 6,937,663 B2 | 8/2005 | Jett et al. |
| 6,937,667 B1 | 8/2005 | Fullerton et al. |
| 6,937,674 B2 | 8/2005 | Santhoff et al. |
| 6,947,492 B2 | 9/2005 | Santhoff et al. |
| 6,950,485 B2 | 9/2005 | Richards et al. |
| 6,954,480 B2 | 10/2005 | Richards et al. |
| 6,959,031 B2 | 10/2005 | Haynes et al. |
| 6,959,032 B1 | 10/2005 | Richards et al. |
| 6,961,285 B2 | 11/2005 | Niemiec et al. |
| 6,963,727 B2 | 11/2005 | Shreve |
| 6,980,613 B2 | 12/2005 | Krivokapic |
| 6,989,751 B2 | 1/2006 | Richards |
| 7,002,473 B2 | 2/2006 | Glick et al. |
| 7,003,289 B1 | 2/2006 | Kolls |
| 7,015,793 B2 | 3/2006 | Gabig, Jr. et al. |
| 7,020,224 B2 | 3/2006 | Krivokapic |
| 7,026,983 B2 | 4/2006 | Spratt |
| 7,027,425 B1 | 4/2006 | Fullerton et al. |
| 7,027,483 B2 | 4/2006 | Santhoff et al. |
| 7,027,493 B2 | 4/2006 | Richards |
| 7,030,806 B2 | 4/2006 | Fullerton |
| 7,039,392 B2 | 5/2006 | McCorkle et al. |
| 7,042,417 B2 | 5/2006 | Santhoff et al. |
| 7,046,187 B2 | 5/2006 | Fullerton et al. |
| 7,046,618 B2 | 5/2006 | Santhoff et al. |
| 7,058,414 B1 | 6/2006 | Rofheart et al. |
| 7,069,111 B2 | 6/2006 | Glenn et al. |
| 7,075,476 B2 | 7/2006 | Kim |
| 7,079,827 B2 | 7/2006 | Richards et al. |
| 7,098,769 B2 | 8/2006 | Ott |
| 7,099,367 B2 | 8/2006 | Richards et al. |
| 7,099,368 B2 | 8/2006 | Santhoff et al. |
| 7,116,266 B1 | 10/2006 | Vesel et al. |
| 7,119,659 B2 | 10/2006 | Bonalle et al. |
| 7,129,886 B2 | 10/2006 | Hall et al. |
| 7,132,975 B2 | 11/2006 | Fullerton et al. |
| 7,139,647 B2 | 11/2006 | Larsen |
| 7,145,954 B1 | 12/2006 | Pendergrass et al. |
| 7,148,791 B2 | 12/2006 | Grisham et al. |
| 7,149,533 B2 | 12/2006 | Laird et al. |

(56) References Cited

U.S. PATENT DOCUMENTS

| | | | |
|---|---|---|---|
| 7,151,490 B2 | 12/2006 | Richards | |
| 7,167,525 B2 | 1/2007 | Santhoff et al. | |
| 7,170,408 B2 | 1/2007 | Taylor et al. | |
| 7,178,719 B2 | 2/2007 | Silverbrook et al. | |
| 7,184,938 B1 | 2/2007 | Lansford et al. | |
| 7,190,722 B2 | 3/2007 | Lakkis et al. | |
| 7,190,729 B2 | 3/2007 | Siwiak | |
| 7,206,334 B2 | 4/2007 | Siwiak | |
| 7,206,559 B2 * | 4/2007 | Meade, II | 455/151.1 |
| 7,209,724 B2 | 4/2007 | Richards et al. | |
| 7,209,753 B2 | 4/2007 | Raith | |
| 7,230,980 B2 | 6/2007 | Langford et al. | |
| 7,239,277 B2 | 7/2007 | Fullerton et al. | |
| 7,245,900 B1 | 7/2007 | Lamb et al. | |
| RE39,759 E | 8/2007 | Fullerton | |
| 7,256,727 B2 | 8/2007 | Fullerton et al. | |
| 7,271,779 B2 | 9/2007 | Hertel | |
| 7,308,356 B2 | 12/2007 | Melaku et al. | |
| 7,310,532 B2 | 12/2007 | Knauerhase et al. | |
| 7,363,494 B2 | 4/2008 | Brainard et al. | |
| 7,366,509 B2 | 4/2008 | Akgun et al. | |
| 7,383,984 B2 | 6/2008 | Silverbrook et al. | |
| 7,398,392 B2 | 7/2008 | Weber | |
| 7,505,443 B2 | 3/2009 | McNew et al. | |
| 7,554,979 B2 | 6/2009 | Ikeda | |
| 7,581,113 B2 | 8/2009 | Smith et al. | |
| 7,724,705 B2 * | 5/2010 | Erola et al. | 370/331 |
| 7,739,157 B2 | 6/2010 | Bonner et al. | |
| 7,783,532 B2 | 8/2010 | Hsu et al. | |
| 7,818,762 B2 | 10/2010 | Liu et al. | |
| 7,870,021 B2 | 1/2011 | Mankoff | |
| 7,870,229 B2 | 1/2011 | Spector | |
| 8,552,903 B2 | 10/2013 | Julian et al. | |
| 2001/0014870 A1 | 8/2001 | Saito et al. | |
| 2001/0042010 A1 | 11/2001 | Hassell | |
| 2002/0002504 A1 | 1/2002 | Engel et al. | |
| 2002/0004783 A1 | 1/2002 | Paltenghe et al. | |
| 2002/0010627 A1 | 1/2002 | Lerat | |
| 2002/0046084 A1 | 4/2002 | Steele et al. | |
| 2002/0065713 A1 | 5/2002 | Awada et al. | |
| 2002/0091569 A1 | 7/2002 | Kitaura et al. | |
| 2002/0091571 A1 | 7/2002 | Thomas et al. | |
| 2002/0107738 A1 | 8/2002 | Beach et al. | |
| 2002/0111140 A1 | 8/2002 | Kim | |
| 2002/0111907 A1 | 8/2002 | Ling | |
| 2002/0116271 A1 | 8/2002 | Mankoff | |
| 2002/0128903 A1 | 9/2002 | Kernahan | |
| 2002/0138345 A1 | 9/2002 | Dickson et al. | |
| 2002/0138346 A1 | 9/2002 | Kodaka et al. | |
| 2002/0169665 A1 | 11/2002 | Hughes et al. | |
| 2002/0169668 A1 | 11/2002 | Bank et al. | |
| 2002/0169892 A1 | 11/2002 | Miyaoku et al. | |
| 2002/0178060 A1 | 11/2002 | Sheehan | |
| 2002/0194303 A1 | 12/2002 | Suila et al. | |
| 2003/0004808 A1 | 1/2003 | Elhaoussine et al. | |
| 2003/0004821 A1 | 1/2003 | Dutta et al. | |
| 2003/0005085 A1 | 1/2003 | Matsuno | |
| 2003/0036378 A1 | 2/2003 | Dent | |
| 2003/0055726 A1 | 3/2003 | Sohya et al. | |
| 2003/0074259 A1 | 4/2003 | Slyman, Jr. et al. | |
| 2003/0093283 A1 | 5/2003 | Morsa | |
| 2003/0093314 A1 | 5/2003 | Leung et al. | |
| 2003/0108009 A1 | 6/2003 | Petersen | |
| 2003/0115152 A1 | 6/2003 | Flaherty | |
| 2003/0117635 A1 | 6/2003 | Roberts | |
| 2003/0158796 A1 | 8/2003 | Balent | |
| 2003/0195806 A1 | 10/2003 | Willman et al. | |
| 2003/0217153 A1 | 11/2003 | Rao et al. | |
| 2003/0220765 A1 * | 11/2003 | Overy et al. | 702/158 |
| 2003/0233190 A1 | 12/2003 | Jones | |
| 2004/0054592 A1 | 3/2004 | Hernblad | |
| 2004/0054732 A1 | 3/2004 | Carter et al. | |
| 2004/0064351 A1 | 4/2004 | Mikurak | |
| 2004/0117250 A1 | 6/2004 | Lubow et al. | |
| 2004/0137886 A1 | 7/2004 | Ross et al. | |
| 2004/0143500 A1 | 7/2004 | Lopez et al. | |
| 2004/0158490 A1 | 8/2004 | Sakamura et al. | |
| 2004/0158492 A1 | 8/2004 | Lopez et al. | |
| 2004/0203963 A1 | 10/2004 | Shivaram et al. | |
| 2004/0218574 A1 | 11/2004 | Sata et al. | |
| 2004/0222302 A1 | 11/2004 | Matsumori | |
| 2004/0233621 A1 | 11/2004 | Maeoka et al. | |
| 2004/0240565 A1 | 12/2004 | Santhoff et al. | |
| 2004/0243519 A1 | 12/2004 | Perttila et al. | |
| 2004/0254836 A1 | 12/2004 | Emoke Barabas et al. | |
| 2005/0004840 A1 | 1/2005 | Wanninger | |
| 2005/0027984 A1 | 2/2005 | Saito et al. | |
| 2005/0038574 A1 | 2/2005 | Gila et al. | |
| 2005/0040230 A1 | 2/2005 | Swartz et al. | |
| 2005/0114213 A1 | 5/2005 | Smith et al. | |
| 2005/0131761 A1 | 6/2005 | Trika et al. | |
| 2005/0132234 A1 | 6/2005 | Dawson | |
| 2005/0135304 A1 | 6/2005 | Wentink et al. | |
| 2005/0138576 A1 | 6/2005 | Baumert et al. | |
| 2005/0184145 A1 | 8/2005 | Law et al. | |
| 2005/0200671 A1 | 9/2005 | Mistry et al. | |
| 2005/0204152 A1 | 9/2005 | Breitbach | |
| 2005/0208925 A1 * | 9/2005 | Panasik et al. | 455/404.1 |
| 2005/0230473 A1 | 10/2005 | Fajkowski | |
| 2005/0237270 A1 | 10/2005 | Adams et al. | |
| 2006/0003776 A1 | 1/2006 | Natori et al. | |
| 2006/0014532 A1 * | 1/2006 | Seligmann et al. | 455/420 |
| 2006/0015404 A1 | 1/2006 | Tran | |
| 2006/0026070 A1 | 2/2006 | Sun | |
| 2006/0030341 A1 | 2/2006 | Pham | |
| 2006/0068822 A1 | 3/2006 | Kalhan | |
| 2006/0073851 A1 | 4/2006 | Colando et al. | |
| 2006/0074784 A1 | 4/2006 | Brown | |
| 2006/0111967 A1 | 5/2006 | Forbes | |
| 2006/0130100 A1 | 6/2006 | Pentland | |
| 2006/0177030 A1 | 8/2006 | Rajagopalan et al. | |
| 2006/0178932 A1 | 8/2006 | Lang | |
| 2006/0180664 A1 | 8/2006 | Barrett et al. | |
| 2006/0194569 A1 | 8/2006 | Hsueh | |
| 2006/0293968 A1 | 12/2006 | Brice et al. | |
| 2007/0017259 A1 | 1/2007 | Cho et al. | |
| 2007/0043626 A1 | 2/2007 | Duvall et al. | |
| 2007/0057051 A1 | 3/2007 | Bortolin et al. | |
| 2007/0061302 A1 | 3/2007 | Ramer et al. | |
| 2007/0087732 A1 | 4/2007 | Hsueh | |
| 2007/0131759 A1 | 6/2007 | Cox et al. | |
| 2007/0136657 A1 | 6/2007 | Blumenthal et al. | |
| 2007/0136775 A1 | 6/2007 | MacKay et al. | |
| 2007/0138270 A1 | 6/2007 | Reblin | |
| 2007/0150339 A1 | 6/2007 | Retter et al. | |
| 2007/0173266 A1 * | 7/2007 | Barnes | 455/456.1 |
| 2007/0174116 A1 | 7/2007 | Keith et al. | |
| 2007/0174259 A1 | 7/2007 | Amjadi | |
| 2007/0182546 A1 | 8/2007 | Virk et al. | |
| 2007/0200671 A1 | 8/2007 | Kelley et al. | |
| 2007/0203792 A1 | 8/2007 | Rao | |
| 2007/0241189 A1 | 10/2007 | Slavin et al. | |
| 2007/0249288 A1 | 10/2007 | Moallemi et al. | |
| 2007/0259690 A1 | 11/2007 | Julian et al. | |
| 2007/0270129 A1 | 11/2007 | Luo | |
| 2007/0276537 A1 | 11/2007 | Walker et al. | |
| 2007/0285306 A1 | 12/2007 | Julian et al. | |
| 2008/0040229 A1 | 2/2008 | Gholston | |
| 2008/0052169 A1 | 2/2008 | O'shea et al. | |
| 2008/0072066 A1 | 3/2008 | Vogler et al. | |
| 2008/0074264 A1 | 3/2008 | Sharpe et al. | |
| 2008/0077484 A1 | 3/2008 | Main et al. | |
| 2008/0120186 A1 | 5/2008 | Jokinen et al. | |
| 2008/0133349 A1 | 6/2008 | Nazer et al. | |
| 2008/0133366 A1 | 6/2008 | Evans et al. | |
| 2008/0154714 A1 | 6/2008 | Liu et al. | |
| 2008/0154827 A1 | 6/2008 | Connors | |
| 2008/0167991 A1 | 7/2008 | Carlson et al. | |
| 2008/0189170 A1 | 8/2008 | Ramachandra | |
| 2008/0208688 A1 | 8/2008 | Byerley et al. | |
| 2008/0221984 A1 | 9/2008 | Abhyanker | |
| 2008/0238615 A1 | 10/2008 | Carpenter | |
| 2008/0240440 A1 | 10/2008 | Rose et al. | |
| 2008/0262928 A1 | 10/2008 | Michaelis | |

(56) References Cited

U.S. PATENT DOCUMENTS

| | | |
|---|---|---|
| 2008/0270231 A1 | 10/2008 | Li et al. |
| 2008/0300970 A1 | 12/2008 | Scheibe |
| 2008/0300984 A1 | 12/2008 | Li |
| 2009/0061884 A1 | 3/2009 | Rajan et al. |
| 2009/0076911 A1 | 3/2009 | Vo et al. |
| 2009/0076912 A1 | 3/2009 | Rajan et al. |
| 2009/0088182 A1 | 4/2009 | Piersol et al. |
| 2009/0098903 A1 | 4/2009 | Donaldson et al. |
| 2009/0108064 A1 | 4/2009 | Fernandes et al. |
| 2009/0164309 A1 | 6/2009 | Mgrdechian et al. |
| 2009/0178144 A1 | 7/2009 | Redlich et al. |
| 2009/0233575 A1 | 9/2009 | Morrison |
| 2010/0153205 A1 | 6/2010 | Retter et al. |
| 2010/0174615 A1 | 7/2010 | Weaver |
| 2010/0185504 A1 | 7/2010 | Rajan et al. |
| 2010/0205043 A1 | 8/2010 | Edwards |
| 2010/0241574 A1 | 9/2010 | Salazar |
| 2010/0257020 A1 | 10/2010 | Bryant et al. |
| 2010/0280960 A1 | 11/2010 | Ziotopoulos et al. |
| 2010/0289640 A1 | 11/2010 | Annamalai |
| 2010/0299224 A1 | 11/2010 | Borom et al. |
| 2011/0028160 A1 | 2/2011 | Roeding et al. |
| 2011/0119132 A1 | 5/2011 | Morton et al. |
| 2011/0215138 A1 | 9/2011 | Crum |
| 2011/0250901 A1 | 10/2011 | Grainger et al. |
| 2011/0276385 A1 | 11/2011 | Keller |

FOREIGN PATENT DOCUMENTS

| | | |
|---|---|---|
| CN | 1672382 | 9/2005 |
| CN | 1694122 A | 11/2005 |
| CN | 1716223 A | 1/2006 |
| CN | 1799061 A | 7/2006 |
| CN | 1879121 A | 12/2006 |
| CN | 101384031 A | 3/2009 |
| EP | 1758308 A1 | 2/2007 |
| EP | 1926335 A1 | 5/2008 |
| JP | 11353555 A | 12/1999 |
| JP | 2000275328 A | 10/2000 |
| JP | 2001034658 A | 2/2001 |
| JP | 2001145785 A | 5/2001 |
| JP | 2001223712 A | 8/2001 |
| JP | 2001325507 A | 11/2001 |
| JP | 2002073666 A | 3/2002 |
| JP | 2002074131 A | 3/2002 |
| JP | 2002109237 A | 4/2002 |
| JP | 2002149945 A | 5/2002 |
| JP | 2002150102 A | 5/2002 |
| JP | 2002525641 A | 8/2002 |
| JP | 2002251555 A | 9/2002 |
| JP | 2002279274 A | 9/2002 |
| JP | 2002291047 | 10/2002 |
| JP | 2002374261 A | 12/2002 |
| JP | 2003006543 A | 1/2003 |
| JP | 2003023367 A | 1/2003 |
| JP | 2003051771 | 2/2003 |
| JP | 2003067606 A | 3/2003 |
| JP | 2003115001 A | 4/2003 |
| JP | 2003187140 A | 7/2003 |
| JP | 2003208381 A | 7/2003 |
| JP | 2003256705 A | 9/2003 |
| JP | 2003263582 A | 9/2003 |
| JP | 2004094543 A | 3/2004 |
| JP | 2004516989 A | 6/2004 |
| JP | 2004220522 A | 8/2004 |
| JP | 2004236166 A | 8/2004 |
| JP | 2004248215 A | 9/2004 |
| JP | 2004272463 A | 9/2004 |
| JP | 2004326303 A | 11/2004 |
| JP | 2004328542 A | 11/2004 |
| JP | 2004362470 A | 12/2004 |
| JP | 2005011318 A | 1/2005 |
| JP | 2005020350 A | 1/2005 |
| JP | 2005045756 A | 2/2005 |
| JP | 2005078173 A | 3/2005 |
| JP | 2005128903 A | 5/2005 |
| JP | 2005128965 A | 5/2005 |
| JP | 2005141686 A | 6/2005 |
| JP | 2005209114 A | 8/2005 |
| JP | 2005528016 A | 9/2005 |
| JP | 2005533316 A | 11/2005 |
| JP | 2005534260 A | 11/2005 |
| JP | 2006011806 A | 1/2006 |
| JP | 2006018511 A | 1/2006 |
| JP | 2006018824 A | 1/2006 |
| JP | 2006020004 A | 1/2006 |
| JP | 2006091355 A | 4/2006 |
| JP | 2006129000 A | 5/2006 |
| JP | 2006139431 A | 6/2006 |
| JP | 2006197458 | 7/2006 |
| JP | 2006227901 A | 8/2006 |
| JP | 2006295249 A | 10/2006 |
| JP | 2007502087 A | 2/2007 |
| JP | 2007072906 A | 3/2007 |
| JP | 2007201851 A | 8/2007 |
| JP | 2007213276 A | 8/2007 |
| JP | 2008225540 A | 9/2008 |
| JP | 2008293123 A | 12/2008 |
| JP | 2009188922 | 8/2009 |
| JP | 2010515168 A | 5/2010 |
| KR | 1020020068945 | 8/2002 |
| KR | 20020096946 A | 12/2002 |
| KR | 20030018741 A | 3/2003 |
| KR | 20040069122 A | 8/2004 |
| KR | 100512362 B1 | 9/2005 |
| KR | 20060014942 A | 2/2006 |
| KR | 20060018235 A | 2/2006 |
| KR | 20060064222 A | 6/2006 |
| KR | 20060124430 A | 12/2006 |
| KR | 20070016301 | 2/2007 |
| RU | 2150790 C1 | 6/2000 |
| RU | 2267156 C2 | 12/2005 |
| RU | 20050100782 | 2/2006 |
| RU | 2301450 C2 | 6/2007 |
| TW | I228364 | 2/2005 |
| TW | I252324 | 4/2006 |
| TW | I252628 | 4/2006 |
| TW | I252639 | 4/2006 |
| TW | I252671 | 4/2006 |
| WO | WO9613920 A1 | 5/1996 |
| WO | 0178423 A1 | 10/2001 |
| WO | 0221478 | 3/2002 |
| WO | WO0225823 | 3/2002 |
| WO | 0250732 A1 | 6/2002 |
| WO | WO02054353 A1 | 7/2002 |
| WO | WO03107289 | 12/2003 |
| WO | 2004008276 A2 | 1/2004 |
| WO | WO-2004014037 A1 | 2/2004 |
| WO | 2005045455 A2 | 5/2005 |
| WO | WO-2005064515 A1 | 7/2005 |
| WO | 2005110208 A1 | 11/2005 |
| WO | 2005122483 A1 | 12/2005 |
| WO | WO2006030341 | 3/2006 |
| WO | 2006092772 | 9/2006 |
| WO | 2007026745 A1 | 3/2007 |
| WO | WO2008027965 | 3/2008 |
| WO | 2008146576 A1 | 12/2008 |
| WO | WO2008157806 | 12/2008 |

OTHER PUBLICATIONS

Bardia Alavi, et al., "Indoor Geolocation Distance Error Modeling using UWB Channel Measurements", 2005 IEEE 16th International Symposium on Personal, Indoor and Mobile Radio Communications, Sep. 11-14, 2005.

"Examples of Judging whether Business-Related Inventions are Patentable" http://www.jpo.go.jp/tetuzuki/t_tokkyo/bijinesu/biz_pat_case.htm.

Okazaki, "Eight Methods for Capitalizing on Access Log Analysis, which are Essential to SEO, Marketing and Redesign", Web Creators, NdN Corporation, Japan, Mar. 1, 2005, vol. 39, pp. 148-155.

Taiwan Search Report—TW096113260—TIPO—Apr. 26, 2011.

(56) References Cited

OTHER PUBLICATIONS

Co-pending U.S. Appl. No. 13/048,060, filed Mar. 15, 2011.
Co-pending U.S. Appl. No. 13/363,580, filed Feb. 1, 2012.
Lester, J et al., ""Are You With Me ?"—Using Accelerometers to Determine if Two Devices are Carried by the Same Person", LNCS, Pervasive Computing, Apr. 2004,vol. 3001, pp. 33-50.
Blundo, C. et al.: "Secure E-Coupons," Electronic Commerce Research, vol. 5, No. 1, pp. 1179-1139, Kluwer, Dordrecth, NL, (Jan. 1, 2005), XP002380651, ISSN: 1389-5753, Section 8.4.
Translation of Office Action in Singapore application 200907742-1 corresponding to U.S. Appl. No. 12/142,159, citing US20060194569, US20040143500, US20020111907 and KR20020068945 dated Feb. 10, 2011.
Written Opinion—PCT/US07/066731, International Search Authority—European Patent Office, Nov. 9, 2007.
Roumeliotis, T., "Five geofencing ideas for mobile marketing from brands and retailers," Mobile Commerce Daily, Jul. 16, 2010, 2 pages, Retrieved from http://www.mobilecommercedaily.com/five-geofencing-ideas-for-mobile-marketing-from-brands-and-retailers.
"Digital Watermarking Alliance", Oct. 19, 2006, 8 Pages, Retrieved from the Internet: URL: http://www.digitalwatermarkingalliance.org/faqs.asp [retrieved on Jul. 21, 2014].
Itao T., "Relationship Mechanism for Dynamic and User Preference-Aware Service Creation", Journal of the Information Processing Society of Japan, Japan, IPSJ, Mar. 15, 2003, vol. 44, No. 3, pp. 812-825.
Kirovski D., et al., "Spread Spectrum Watermarking of Audio Signals", IEEE Transactions on Signal Processing, vol. 51, No. 4, pp. 1020-1033, Apr. 2003.

\* cited by examiner

DISTANCE-BASED ASSOCIATION

CLAIM OF PRIORITY UNDER 35 U.S.C. §119

This application claims the benefit of and priority to U.S. Provisional Patent Application No. 60/792,035, filed Apr. 14, 2006, which is assigned to the assignee hereof, and the disclosure of which is hereby incorporated by reference herein.

CROSS-REFERENCE TO RELATED APPLICATION

This application is related to concurrently filed and commonly owned U.S. patent application Ser. No. 11/692,097, entitled "DISTANCE-BASED PRESENCE MANAGEMENT," the disclosure of which is hereby incorporated by reference herein.

BACKGROUND

1. Field

This application relates generally to wireless communication, and more specifically, to distance-based functionality in a wireless communication system.

2. Background

In a wireless communication system various provisions may be made to enable two or more wireless devices to communicate with one another and, in some applications, to enable one wireless device to access functionality provided by another wireless device. For example, when a wireless device enters a coverage area of another wireless device, the wireless devices may perform an association operation to enable the two devices to communicate with one another. In addition, other related operations such as presence management may be performed to enable a wireless device to affect the operation of another wireless device.

Examples of association include setting up a wireless laptop and an wireless access point to communicate or setting up communication between a wireless cell phone or entertainment device (e.g., an MP3 player) and a peripheral device such as a wireless headset (e.g., headphones, an ear piece, etc.) or watch. Briefly, association may involve exchanging messages that enable the wireless devices to determine whether they are capable of communicating with one another and whether they are authorized to do so. For example, the wireless devices may exchange messages that indicate their respective capabilities. In conjunction with this procedure, the wireless devices may negotiate or cooperate in some other manner to agree on a set of parameters to be used for communicating. Moreover, in some applications the wireless devices may utilize an authentication procedure of some type to verify the identity of each other. This identity information may be used by the wireless devices to, for example, determine whether they are authorized to communicate with one another.

Various operations may be performed to enable or otherwise facilitate association. For example, some applications may employ signal strength-based association where it is assumed that the wireless devices are close enough to associate if a received signal strength exceeds a threshold. Other applications may employ RFID-related technology whereby wireless devices are allowed to associate with another if they are close enough so that one device induces RF energy in another device.

In some applications a wireless device may employ presence management to provide certain functionality based on the proximity of the wireless device to another device. For example, in some applications presence management may be employed to modify a user interface of a computer based on which user is sitting in front of the computer. Presence management also may be used to modify the characteristics of a room (e.g., lighting, temperature, music, etc.) based on who is in the room.

In practice, an operation such as association or presence management may involve some user interaction with the wireless device to initiate or complete the operation. For example, during association a user may manually set each wireless device into an association or discovery mode, navigate through some software interfaces to a list of discovered wireless devices, select a wireless device, and potentially input some information about the wireless device. In a typical example, information to be entered by a user may include authentication codes or multiple access code information. Similarly, during presence management a user may press a configuration button (e.g., associated with a car seat, a home theater system, etc.), type in a username and password, insert a card, or invoke wireless detection of the presence of a device.

In practice, operations such as association and presence management may not provide a desired level of functionality or may be inconvenient for a user. For example, presence management may be relatively course in nature in that it simply involves determine whether a connection with another wireless device may be detected. In addition, the steps performed by a user to accomplish association, presence management, or other operations (e.g., as mentioned above) may be relatively complicated and confusing for the user. Consequently, a need exists for alternative methods for performing such operations.

SUMMARY

A summary of sample aspects of the disclosure follows. For convenience, one or more aspects of the disclosure may be referred to herein simply as "some aspects."

This application relates in some aspects to performing an act based on at least one distance between devices. For example, one of various techniques may be employed to determine a distance-related function such as distance or relative motion between two devices. A determination may then be made as to whether the determined distance function meets specified criteria. If so, a corresponding action may then be taken.

In some aspects association between two or more devices may be based on one or more determined distances. For example, an association procedure may be initiated or facilitated in some manner by determining whether the devices are within a given range of one another and/or are moved with respect to one another in a certain manner.

Distance-based association may be employed in a variety of use cases. For example, in a personal or body area network a large number of different piconets may be owned and managed by different entities (e.g., people or networked devices). Moreover, these piconets may have different associated power level requirements and data rates that overlap. Through the use of distance-based association, a new device entering the network may be efficiently associated with a desired piconet or other device in the network. For example, devices may be associated with one another if they are within one foot of each other. Similarly, if several devices are close to one another, the closest devices (e.g., the two closest devices) of these devices may be associated with one another. In addition, distance-based association may be employed to provide secure communication, such as in a point-of-sale application where the relative proximity of two devices is used to ensure that the two devices are authorized to conduct a transaction.

In some aspects presence management may be based on one or more determined distances. Here, various presence management operations may be invoked if it is determined that two or more devices are within a given range of one another and/or are moved with respect to one another in a certain manner. As an example, distance-based presence management may enable a user in possession of a presence management-enabled device to be presented with different presence management responses as the user moves closer to or further away from another presence management-enabled device. Similarly, distance-based presence management may enable a user that is walking through a room to be presented with a different presence management response as opposed to when the same user stops in the room or when the user remain seated in the room.

A distance-related function as taught herein may take various forms. For example, such a function may relate to a distance between devices, two or more distances between devices if the devices are moved with respect to one another, a rate of change in the relative distance between devices, relative acceleration between devices, some other distance-related function, or some combination of two or more of the these distance-related functions.

A distance-related function as taught herein may be implemented in various ways. For example, a distance may be measured by determining the amount of time it takes for signals to travel from one device to another device and then back (e.g., a round-trip time). Such a round-trip time may be calculated, for example, using two-way ranging or by sending interrogation and response signals between the devices. A distance also may be determined using a time-of-arrival measurement or a received power measurement. A rate of change in relative distance may be determined through the use of, for example, a time-of-arrival measurement, a received power measurement, acceleration readings, imaging techniques, detection of changes in electrical and magnetic fields, or detection of Doppler shifts. Relative acceleration between devices may be determined from the rate of change in relative distance data.

BRIEF DESCRIPTION OF THE DRAWINGS

These and other features, aspects and advantages of the disclosure will be more fully understood when considered with respect to the following detailed description, appended claims and accompanying drawings, wherein:

Figure 1:
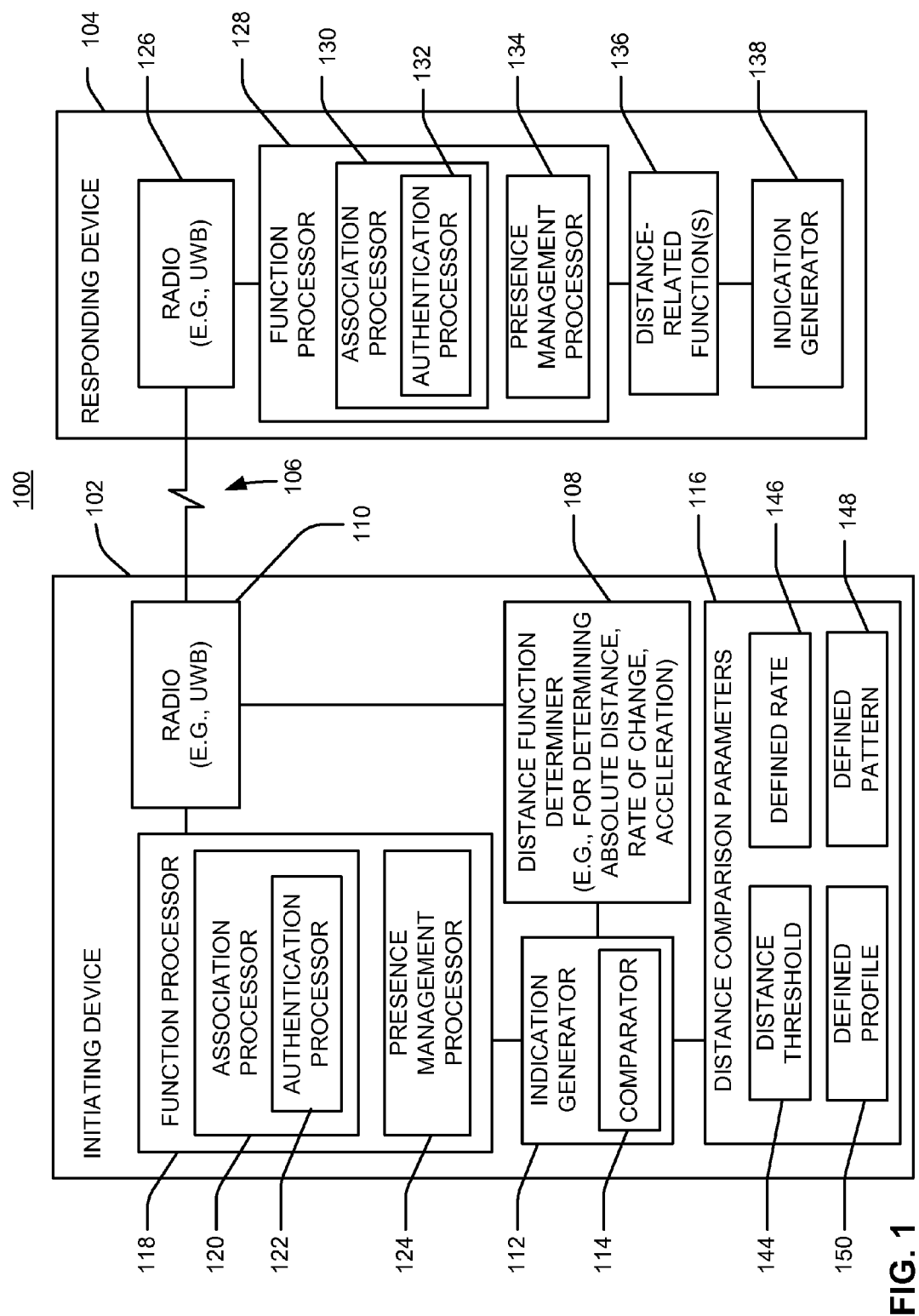
FIG. 1 is a simplified block diagram of several sample aspects of a communication system adapted to perform distance-based operations.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus (e.g., device) or method. Finally, like reference numerals may be used to denote like features throughout the specification and figures.

DETAILED DESCRIPTION

Various aspects of the disclosure are described below. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein. As an example, in some aspects a distance-related function as taught herein may relate to a one distance, while in other aspects a distance-related function may relate to a distance and a rate of change of distance.

FIG. 1 illustrates certain aspects of a communication system 100 where a first device 102 may communicate with a second device 104 via a wireless communication link 106. As an example, the device 102 may enter a wireless coverage area of the device 104 and various provisions may then be taken as discussed below to enable the devices 102 and 104 to communicate. In particular, the devices 102 and 104 include functionality whereby operations such as association and presence management are initiated, terminated, or performed in accordance with one or more distance relationships between the devices 102 and 104.

The devices 102 and 104 in the example of FIG. 1 are depicted in a simplified manner to emphasize certain components that may provide functionality relating to distance determination and associated processing. Specifically, the device 102 is depicted to emphasize components that may be employed in a device that ultimately determines one or more distances between the devices 102 and 104 and performs one or more operations based on that determination. Conversely, the device 104 is depicted to emphasize components that may be employed in a device that may perform operations in conjunction with the distance determining device. As will be discussed in more detail below, the device 104 may include functionality that facilitates the distance determination by the device 102 and may also perform one or more operations based on that determination. It should be appreciated that a given device may incorporate the functionality depicted for device 102, the functionality depicted for device 104, or some combination thereof.

The device 102 includes a distance function determiner component (hereafter, distance determiner 108) that is adapted to perform various functions relating to determining one or more distance-related parameters. For example, the distance determiner 108 may determine an absolute distance between the devices 102 and 104, two or more distances between the devices 102 and 104 (e.g., in the event the devices 102 and 104 are moved with respect to one another), a rate of change in the relative distance between the devices 102 and 104, relative acceleration between the devices 102 and 104, or some other distance-related function. As will be discussed in more detail below, the distance determiner 108 may thus include appropriate components or may cooperate with one or more other components (e.g., a radio 110) to repeatedly determine the distance between the devices 102 and 104.

The device 102 also includes an indication generator 112 that is adapted to generate an indication relating to the determined distance parameter(s). For example, the indication generator 112 may generate an indication of the determined absolute distance(s), rate of change in relative distance, relative acceleration, etc. In addition, the indication generator 112 may include a comparator 114 that compares a determined distance with a distance comparison parameter 116 (e.g., a threshold) that may be maintained in the device 102 (e.g., in a data memory). The indication generator 112 may then generate a comparison result indication in accordance with the comparison. As an example, the comparison result indication may indicate that a determined distance is less than a threshold.

The device 102 includes a processor component 118 that is adapted to perform various functions based on at least one determined distance. For example, the processor component 118 may invoke one or more operations depending on the value of the indication. In addition, or in the alternative, the operations performed by the processing component may utilize the indication in some manner.

In the example of FIG. 1 the processor component 118 provides functionality relating to association (e.g., including authentication) and presence management. For example, an association procedure, an authentication procedure, or both, may be invoked or may be dependent on a given distance-related relationship between the devices 102 and 104. Similarly, a presence management procedure may be invoked or may be dependent upon a given distance-related relationship between the devices 102 and 104. To provide such functionality, the processor component 118 may include an association processor component 120, an authentication processor component 122, and a presence management processor component 124.

The device 104 may include several components that operate in conjunction with corresponding components of device 102. For example, the device 104 may include a radio 126 adapted to communicate via one or more wireless communication links (e.g., the link 106) with one or more wireless devices (e.g., the radio 110 of the device 102). The device 104 also may include a processor component 128 that provides functionality that is complementary to the functionality of the processor component 118. Accordingly, the processor component 128 may include an association processor 130, an authentication processor 132, and a presence management processor 134. The device 104 also may include a distance function component 136 for performing one or more distance-related functions in conjunction with the distance determiner 108. Also, the device 104 may include an indication generator 138 that may generate, for example, distance-related indications used by the device 104 or the device 102.

The devices 102 and 104 may take various forms. For example, in some aspects the devices 102 and 104 may comprises various combinations of a headset, a microphone, a medical device, a biometric sensor, a heart rate monitor, a pedometer, an EKG device, a user I/O device, a watch, a remote control, a switch, a tire pressure monitor, an entertainment device, a computer, a point-of-sale device, a hearing aid, a set-top box, a cell phone, or some other device with some form of wireless signaling capabilities. In some aspects the device 104 may comprises an access device (e.g., a Wi-Fi access point) for a communication system. For example, the device 104 may provide connectivity to another network (e.g., a wide area network such as the Internet) via a wired or wireless communication link. Accordingly, the device 104 may enable the device 102 (e.g., a Wi-Fi station) to access the other network. In addition, it should be appreciated that one or both of the devices 102 and 104 may be portable or, in some cases, relatively non-portable.

The devices 102 and 104 may include various components that perform functions bases on signals transmitted or received via the wireless communication link. For example, a headset may include a transducer adapted to provide an audible output based on a signal received via the wireless communication link. A watch may include a display adapted to provide a visual output based on a signal received via the wireless communication link. A medical device may include a sensor adapted to generate sensed signals to be transmitted via the wireless communication link.

The devices 102 and 104 may support or otherwise use various wireless communication links and wireless network topologies. For example, in some aspects the devices 102 and 104 may comprise or form part of a body area network or a personal area network (e.g., an ultra-wideband network). In addition, in some aspects the devices 102 and 104 may comprise or form part of a local area network or a wide area network. The devices 102 and 104 also may support or otherwise use one or more of a variety of wireless communication protocols or standards including, for example, CDMA, TDMA, OFDM, OFDMA, WiMAX, Wi-Fi, and other wireless technologies. Accordingly, the devices 102 and 104 may include appropriate components to establish one or more communication links using various wireless technologies.

Figure 2:
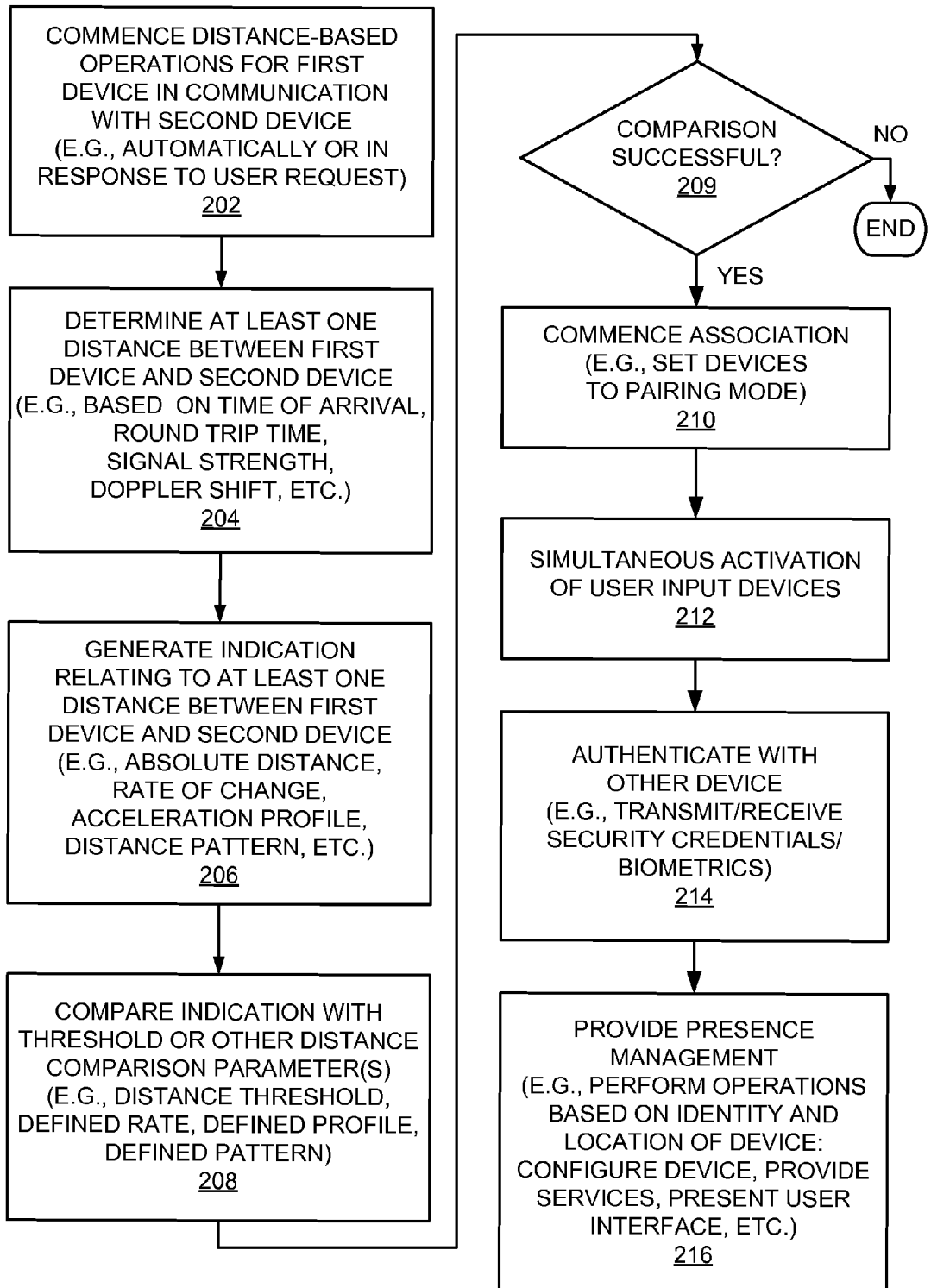
FIG. 2 is a flowchart of several sample aspects of operations that may be performed by a device to perform distance-based operations.
Figure 3:
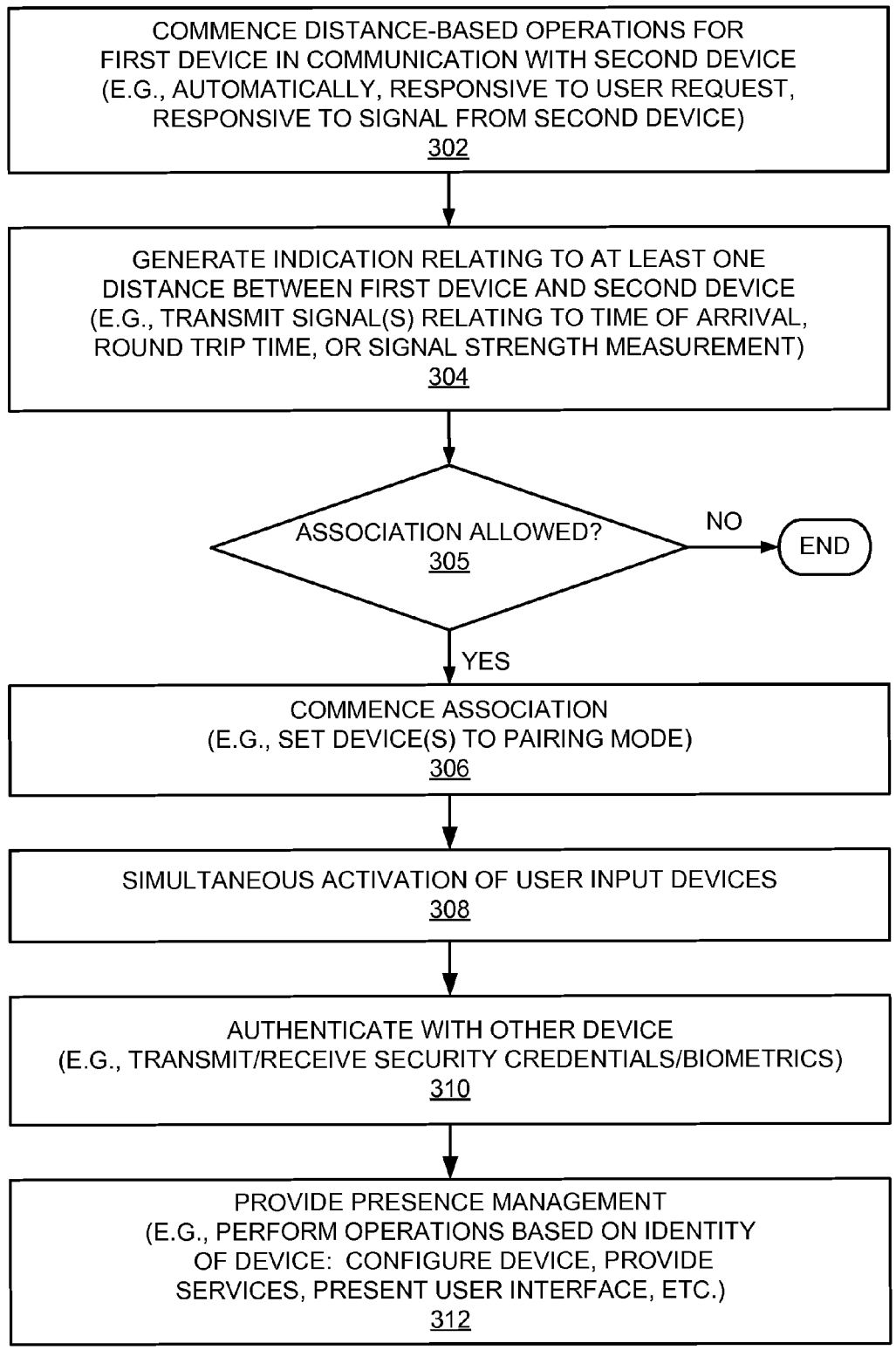
FIG. 3 is a flowchart of several sample aspects of operations that may be performed by a device to perform distance-based operations.
Figure 4:
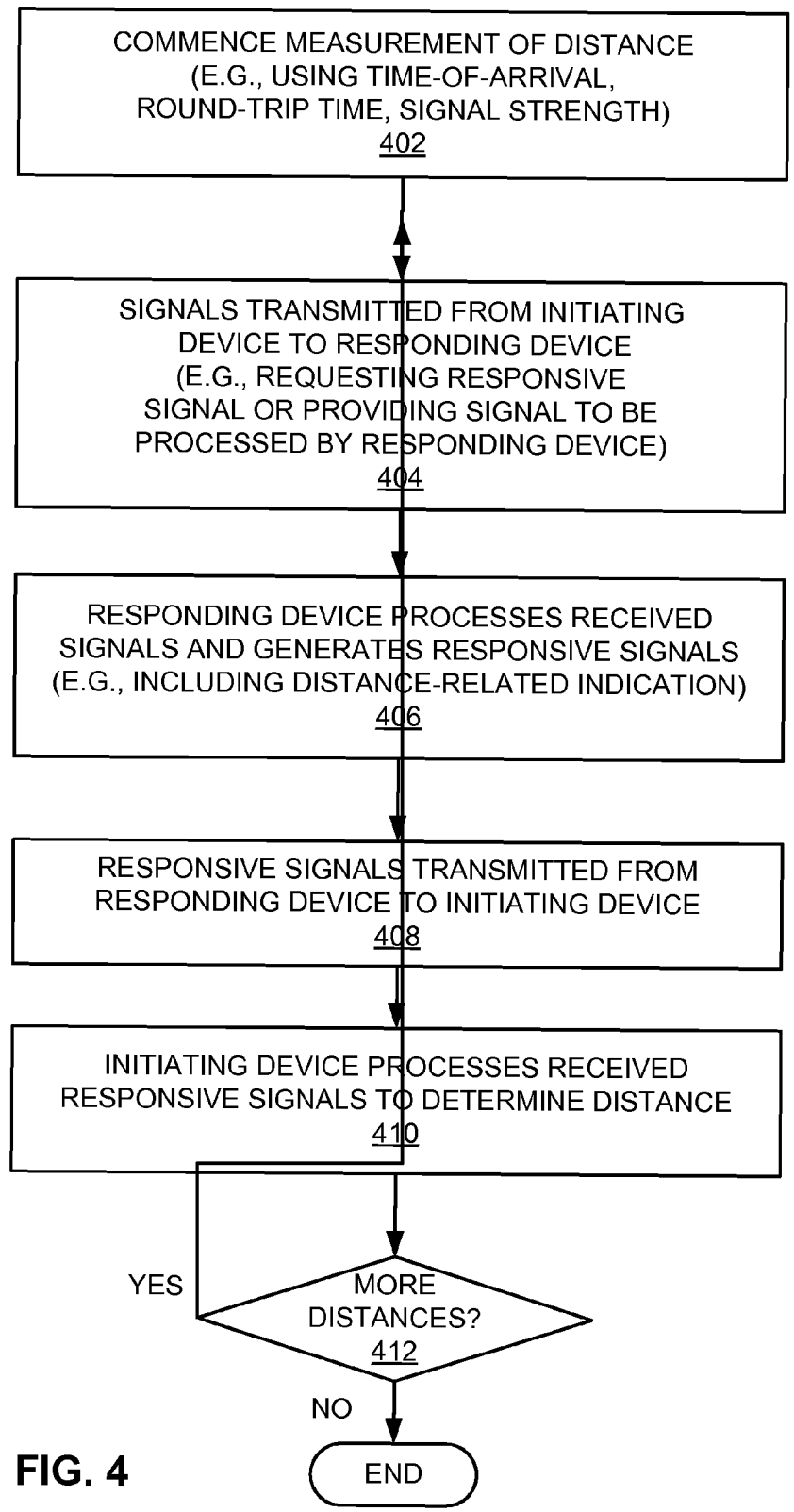
FIG. 4 is a flowchart of several sample aspects of operations that may be performed by devices to determine at least one distance.

Sample operations of the system 100 will now be discussed in more detail in conjunction with the flowcharts of FIGS. 2, 3 and 4. FIG. 2 relates to operations that may be performed, for example, by the device 102. FIG. 3 relates to operations that may be performed, for example, by the device 104. FIG. 4 relates to operations that may be performed to determine one or more distances between the devices 102 and 104. For convenience, the operations of FIGS. 2, 3, and 4 (or any other operations discussed herein) may be described as being performed by specific components (e.g., devices 102 and 104). It should be appreciated, however, that these operations may be performed in conjunction with and/or by other components and, in some cases, using a different number of components. It also should be appreciated that one or more of the operations described herein may not be employed in a given implementation.

Referring initially to FIG. 2, as represented by block 202 a first device such as device 102 commences distance-based operations (e.g., enables a ranging mode) in conjunction with establishing communication with a second device such as device 104. Here, the device 102 may determine whether it has entered a wireless coverage area associated with the device 104. These operations may be initiated automatically or may be initiated based an action by a user who wishes to associate the device 102 with the device 104. In the former case, a discovery mode may be continually enabled such that the device 102 may repeatedly scan to determine whether it has entered a coverage area of a wireless network (e.g., a body area network or personal area network) or a coverage area of some other wireless device. In the latter case, the user may utilize (e.g., actuate) an input device of the device 102 to initiate a discovery mode that causes the device 102 (e.g., the radio 110) to commence scanning for nearby wireless networks or wireless devices. In conjunction with the operations of block 202, the user may bring the device 102 within a certain range of the device 104.

Referring to FIG. 3, the device 104 also may perform operations that are similar and/or complementary to the operations of block 202. For convenience, the sample operations of FIG. 3 are depicted from the perspective of a first device. In other words, in the context of FIG. 3 the first device may comprise the device 104 and the second device may comprise the device 102 (in contrast with the corresponding relationships described above in conjunction with FIG. 2).

As represented by block 302, the device 104 also may commence distance-based operations by, for example, attempting to discover nearby wireless devices. As discussed above, this may be initiated automatically or in response to some action by the user (e.g., utilizing an input device of the device 104). In addition, or in the alternative, the device 104 may commence a discovery procedure in response to a signal received from the device 102. It should be appreciated that other techniques may be employed to commence discovery or some other similar procedure for initiating communication between devices such as devices 102 and 104.

Referring again to FIG. 2, as represented by block 204 the device 102 (e.g., the distance determiner 108) determines at least one distance between the devices 102 and 104. To this end, the device 102 may receive and process one or more signals from the device 104. In addition, the device 102 may generate various signals and transmit the signals to the device 104. As represented by blocks 206 and 208, the device 102 (e.g., the indication generator 112) may generate one or more indications corresponding to the one or more determined distances. The operations of blocks 204-208 may be invoked in conjunction with invoking the operations of block 202. Thus, these operations may be invoked automatically or in response to some action on the part of a user of the device 102.

As represented by block 304 of FIG. 3, the device 104 may perform operations that are similar and/or complementary to the operations of blocks 204-208. For example, the device 104 (e.g., the indication generator 138) may generate an indication relating to the at least one distance between the device 104 and the device 102. To this end, the device 104 (e.g., the distance function component 136) may perform one or more operations relating to determining the distance between the devices 104 and 102. For example, the distance function component 136 may process one or more signals received from the device 102 relating to a distance determination operation. The component 136 may then generate one or more responsive signals and transmit the signals back to the device 102.

One or more of various techniques may be employed to determine a distance between the devices 102 and 104. For example, in some implementations distance may be measured using time-of-arrival measurements, round-trip time measurements, signal strength measurements, Doppler shift measurements, or some other suitable technique. Several examples of techniques for measuring distance will be discussed in conjunction with FIG. 4, commencing at block 402.

As represented by block 404, in some implementations a device such as the device 102 that initiates the distance measurement operations sends one or more signals to a responsive device such as device 104. For example, the initiating device may send a message to a responding device instructing the other device to send one or more signals back to the initiating device. Thus, in the example of FIG. 1 the distance determiner 108 of the device 102 may cooperate with a transmitter of the radio 110 to transmit appropriate signals to the device 104.

As represented by block 406, the responding device may process the received signals and generate responsive signals (e.g., forming a message). In FIG. 1 the distance function component 136 may cooperate with a receiver of the radio 126 to receive the signals from the device 102.

As represented by block 408, the responsive signals are then transmitted from the responding device to the initiating device. In FIG. 1 the distance function component 136 and the indication generator 138 may thus cooperate with the radio 126 (e.g., the transmitter) to transmit the signals to the device 102.

As represented by block 410, the initiating device processes the received responsive signals, as necessary, to determine a distance between the initiating and responding devices. In FIG. 1 the distance function component 108 may again cooperate with the radio 126 (e.g. the receiver) to receive the signals from the device 104.

Block 412 represents that the above operations may be repeated if there is another distance measure to be taken. Here, it should be appreciated that multiple distance determinations may be made concurrently, in a sequential manner, or in some other manner.

Sample operations of blocks 404 through 410 will now be discussed in more detail in conjunction with specific examples relating to time-of-arrival measurements, round-trip time measurements and signal strength measurements. It should be appreciated that these are but a few of the measurement techniques that may be employed and that the teachings herein may be used in conjunction with other measurement techniques.

In some implementations utilizing time-of-arrival to determine distance the initiating device may measure the times-of-arrival of signals received from the responding device. For example, at block 404 the initiating device (e.g., the distance determiner 108) may request that the responding device transmit several signals to be used for time-of-arrival measurements. At blocks 406 and 408, the responding device may then generate appropriate signals and transmit them to the initiating device. For example, the distance function component 136 and the indication generator 138 may cause the radio 126 to transmit appropriate signals to the radio 110. Then, at block 410 the initiating device (e.g., the distance determiner 108) may perform time-of-arrival measurements and, based on these measurements, determine the distance between the initiating device and the responding device.

In some implementations the responding device may determine the distance between the devices by performing time-of-arrival measurement operations on signals received from the initiating device. In this case, at block 404 the initiating device (e.g., the distance determiner 108 in conjunction with a transmitter of the radio 110) may transmit signals to be used for the time-of-arrival measurements to the responding device. At block 406 the responding device (e.g., the distance function component 136) may perform time-of-arrival measurements and, in some cases, determine the distance between the responding device and the initiating device based on these measurements. In this case, the indication generator 138 may generate an indication relating to the derived distance-related information. At block 408 the responding device (e.g., the indication generator 138) may send the results of the time-of-arrival measurements or the determined distance to the initiating device. At block 410 the initiating device (e.g., the distance determiner 108) may process the received information to provide a determined distance between the devices 102 and 104 for subsequent operations.

In some implementations utilizing round-trip time measurements the initiating device (device 102) may transmit a message to the responding device at a given time (block 404). At block 406 the distance function component 136 may determine the amount of time between receipt of the request signal by the device 104 and the transmission of a responsive signal by the device 104 (i.e., a turnaround time). Alternatively, in cooperation with the radio 126, the distance function component 136 may ensure that a response signal is transmitted within a defined a turnaround time. The device 104 may thus generate a responsive message (e.g., including an indication of the turnaround time as generated, in some cases, by the indication generator 138) and transmit the message to the device 102 (block 408). At block 410 the device 102 may process the received responsive signal to calculate the round-trip time and, in turn, a distance between the devices 102 and 104. To this end, the distance determiner 108 may determine (e.g., in cooperation with the radio 110) the point in time at which the responsive message was received at the device 102. The distance determiner 108 may then determine the round-trip time from the time elapsed between the transmission of the signal at block 404 to the reception of the responsive signal at block 410, excluding the turnaround time of the device 104 supplied with the responsive message.

In some implementations utilizing received signal strength to determine distance the initiating device may measure the signal strength of signals received from the responding device. For example, at block 404 the initiating device (device 102) may transmit a message to the responding device requesting that the responding device transmit a signal at a known signal strength (e.g., a constant energy level). At block 406, in response to the received signal the responding device (e.g., the distance function component 136 in cooperation with indication generator 138) may cause the radio 126 to transmit an appropriate signal or signals to the device 102 (block 408). At block 410, the distance determiner 108 may then calculate the distance between the devices 102 and 104 based on the strength of the corresponding signal(s) received by the radio 110.

In some implementations utilizing received signal strength to determine distance the responding device may measure the signal strength of signals received from the initiating device. In the example of FIG. 1 the device 104 may receive one or more signals having a known signal strength from the device 102 at block 404. In this case, at block 406 the distance function component 136 may calculate the distance between the devices 104 and 102 based on the strength of the signal(s) received by the radio 126. At block 408, the indication generator 138 may send an indication relating to the derived distance information back to the device 102. At block 410 the initiating device (e.g., the distance determiner 108) may then process the received information to provide a determined distance between the devices 102 and 104 for subsequent operations.

Referring again to block 206 of FIG. 2, the device 102 (e.g., the indication generator 112) generates an indication relating to the at least one determined distance generated at block 204. As discussed above, the distance determination and indication generation operations may involve determining one or more distance-related parameters including, for example, a distance between the devices 102 and 104, two or more distances between the devices 102 and 104, a rate of change in the relative distance between the devices 102 and 104, and relative acceleration between the devices 102 and 104. Here, a rate of change in distance (e.g., relative velocity) between the devices 102 and 104 may be determined, for example, by determining a distance between the devices at one point in time, determining a distance between the devices at one or more other points in time, and calculating the change(s) in distance over the associated time period(s). Similar information may be utilized to determine relative acceleration between the devices 102 and 104 using known techniques such as taking a derivative of the rate of change information. It should be appreciated that an indication relating to at least one distance may take a form other than those explicitly mentioned herein.

In some aspects the indication may simply specify a single determined distance between the devices 102 and 104. As will be discussed in more detail below, this form of indication may be compared with one or more threshold distances to determine whether the devices 102 and 104 are separated by a distance that is deemed acceptable for performing some function.

An indication also may specify several determined distances between the devices 102 and 104. For example, the distance between the devices 102 and 104 may be checked at various times. Such an operation may be performed in conjunction with different types of distance determination scenarios.

For example, in some aspects a distance between devices may be checked more than once to provide a more accurate distance reading. Here, clearly erroneous readings may be discarded. In addition, in some cases an average determined distance may be calculated or a mean determined distance and a standard deviation may be calculated. Accordingly, in this scenario the indication may comprise several similar determined distances, a determined distance along with a standard deviation of the determined distances, a range of the determined distances, or some other similar information.

In some aspects multiple distance readings may be employed in a scenario where performance of an operation is predicated on the devices 102 and 104 being moved in a defined pattern with respect to one another. For example, the devices 102 and 104 may initially be placed a first distance apart, then placed a second distance apart, and so forth. Accordingly, in this scenario the indication may comprise a pattern of several determined distances.

In some aspects multiple distance readings may be employed to determine a rate of change in relative distance between the devices 102 and 104. For example, a first distance between the devices may be determined at a first point in time and a second distance between the devices determined at a second point in time. A rate of change in distance may then be determined, for example, by calculating the ratio of the change in distance (e.g., first distance minus second distance) to the elapsed time (e.g. second point in time minus first point in time). Thus, in this scenario the indication may comprise the determined rate of change in relative distance (e.g., an indication of relative velocity).

In some aspects multiple readings of the rate of change in relative distance may be employed. For example, performance of an operation may be predicated on the rate of change in distance (e.g., relative velocity) between the devices 102 and 104 being changed in a defined pattern. Here, the devices 102 and 104 may be moved with respect one another at different velocities over different time periods. In this scenario the indication may comprise a plurality of different rates of change in relative distance.

Similarly, multiple readings of the rate of change in relative distance may be utilized to obtain a profile of the relative acceleration between the devices 102 and 104. For example, acceleration information may be obtained by taking the derivative of relative velocity information collected over a period of time. Thus, in this scenario the indication may comprise the determined relative acceleration at a given point in time.

In a similar manner as discussed above, multiple acceleration readings may be employed where the performance of an operation is predicated on the relative acceleration between the devices 102 and 104 being changed in a defined pattern. Thus, in this scenario the indication may comprise an acceleration profile defining a plurality of relative accelerations.

In some aspects a device may determine several types of distance-related parameters. For example, the device 102 may determine an absolute distance between the devices 102 and 104 and may determine a rate of change in relative distance between the devices 102 and 104. Here, it should be appreciated that in some aspects different distance measurement techniques may be employed to measure these different types of distance-related parameters. For example, a given measurement technique may determine a certain type of distance measurement more effectively than other measurement techniques.

As represented by block 208, the indication generated at block 206 is compared with one or more distance comparison parameters 116 (FIG. 1). The nature of the comparison operation depends on the particular form of the indication.

For example, if an indication relating to a single distance was generated at block 206, this form of indication may be compared with one or more distance thresholds 144 to determine whether the devices 102 and 104 are separated by a distance that is within a range of distances deemed acceptable for performing some function. For example, initiation of a function may be predicated on the devices being less than or more than a certain distance apart (e.g., 1 meter, 3 meters, etc.). Alternatively, initiation of a function may be predicated on the devices being separated by a distance that falls within a range defined by two distance thresholds 144.

In some aspects more than one level of functionality may be defined whereby different levels of functionality are employed based on different distances between the devices 102 and 104. Here, one type of functionality may be employed in the event the determined distance falls within one range (e.g., the devices 102 and 104 are relatively close to one another) while another type of functionality may be employed in the event the determined distance falls within another range (e.g., the devices 102 and 104 are further apart from one another). In this case, the determined distance may be compared to one, two, or more distance thresholds 144.

As noted above, if several indications relating to several distances were generated at block 206, these indications may be compared with one or more distance thresholds 144. In some implementations the distance thresholds 144 may relate to a pattern of distances where the distance between devices is to be changed between various distances in a defined pattern 148. In practice, a tolerance may be associated with each distance threshold of the pattern 148 to account for relatively minor deviations between the determined distances and the defined pattern 148.

If an indication relating to a rate of change in relative distance was generated at block 206, this indication may be compared with a defined rate of change 146. The defined rate of change 146 may comprise, for example, an upper threshold for the rate of change, a lower threshold for the rate of change, a range of rates of change, or a defined pattern 148 of rates of change. As an example of the latter scenario, the ranging criteria may specify that the rate of change between devices is to be changed between various rates of change in a defined pattern 148. Again, a tolerance may be associated with each defined rate of change in the defined a pattern 148 to account for relatively minor deviations between the determined rates of change and the defined pattern 148.

If an indication relating to relative acceleration was generated at block 206, this indication may be compared with a defined acceleration profile 150. The defined acceleration profile 150 may comprise, for example, an upper threshold for acceleration, a lower threshold for the acceleration, a range of accelerations, or a pattern of accelerations. As an example of the latter scenario, the ranging criteria may specify that the relative acceleration between devices is to be changed between accelerations according to a defined acceleration profile 150 (e.g., in a known pattern). Similar to the above scenarios, a range of tolerance may be associated with the accelerations of the defined acceleration profile 150 to account for relatively minor deviations between the determined accelerations and the defined acceleration profile 150.

It should be appreciated that the comparisons of block 208 may be implemented in various ways. For example, the determined distance may simply be subtracted from a distance comparison parameter. In addition, in some implementation multiple comparisons may be made. Such an approach may be used, for example, when the distance is repeatedly checked for a period of time, when several measurements are made to reduce transient conditions, to perform operations relating to a rate of change in relative distance or to relative acceleration, or when a combination of two or more types of determined distances are employed. As an example of the latter scenario, as will be discussed in more detail below an operation may be invoked or modified based on the rate of change in relative distance between devices as well as the absolute distance between the devices.

In conjunction with the operations of block 208, the indication generator 112 may generate a comparison result indication that is indicative of the results of the comparison or some other similar operation. For example, such an indication may indicate that a device did or did not meet the desired criteria for performing a distance-based operation.

As represented by block 209, the device 102 may then take appropriate action based on the results of the comparison. For example, if the comparison result indication indicates that distance criteria have (or a distance criterion has) been met, the device 102 may invoke or terminate a given function or alter the operation of a function in some manner. If the comparison of block 208 is not successful, the operations of FIG. 2 may terminate, and then be invoked at some other point in time.

As represented by block 210, in some implementations distance-based criteria may be used as a prerequisite for commencing association-related operations. For example, if the distance between the devices 102 and 104 is less than a threshold value and/or if the devices 102 and 104 are moved in a proper manner with respect to one another, the device 102 may commence an association procedure with device 104. In addition, as represented by blocks 305 and 306 of FIG. 3, the device 104 may perform operations that are similar and/or complementary to the operations of blocks 209 and 210. Thus, if an association operation is allowed (e.g., based on receipt of a message from the device 102 indicating a successful comparison at block 208), the device 104 may commence association operations in cooperation with the device 102. In some aspects association may be automatically invoked if the devices are within a given distance of one another and/or are moved in a certain manner with respect to one another.

Although block 210 follows blocks 204 through 208 in the example of FIG. 2, these operations are not necessarily performed in the illustrated order. For example, in some implementations the distance determining operations may be performed after the commencement of an association procedure. Thus, one or more distance-related functions as taught herein may be invoked as part of an association procedure. In addition, in some implementations distance determining operations may serve as both a prerequisite to an association procedure and form a part of an association procedure.

In some aspects an association procedure may involve pairing the devices 102 and 104 to enable certain types of communication between the devices 102 and 104. For example, the association procedure may involve establishing application-level communication among the devices 102 and 104.

A variety of operations may be performed in conjunction with an association procedure or in conjunction with some other distance-based operation. For example, blocks 212 and 214 in FIG. 2 and blocks 308 and 310 in FIG. 3 illustrate several procedures that may optionally be invoked in conjunction with the association procedures of blocks 210 and 306, respectively.

As represented by block 212, in some applications an association procedure (e.g., a pairing process) may employ a human synchronization test. For example, such a test may be based on a human synchronization ability whereby a given person may easily actuate two switches substantially simultaneously, yet it may be very difficult for an onlooker to anticipate the right time to actuate a switch at substantially the same time as another person. Accordingly, the operations of block 212 may involve instructing the user (e.g., via a visual command on a display, via a specific configuration of lighting elements such as LEDs, or via an audio command) to simultaneously activate input devices (e.g., actuate switches) on the devices 102 and 104. The association procedure may thus involve determining whether a switch on the device 102 is actuated (e.g., depressed and/or released) at substantially the same time as a switch on the device 104 is actuated. As represented by block 308 of FIG. 3, the device 104 may perform operations that are similar and/or complementary to the operations of block 212. As will be discussed in more detail below, a variety of user input devices (e.g., other than switches) may be used for this operation.

The synchronization test may be implemented in a variety of ways. For example, in some implementations the device 102 may compare the times that the respective switches on the devices 102 and 104 are depressed, the times that the respective switches on the devices 102 and 104 are released, or both. In some implementations the synchronization test may involve multiple actuations of the switches. For example, the user may pick several random timings to simultaneously press and release the buttons on each device. In this case, each device will generate a sequence of times associated with the actuations of its switch. The device 102 may then compare the timings of the sequences in an attempt to determine whether the same person actuated the switches on the devices 102 and 104. In either of the above implementations, if the actuation timings from the devices 102 and 104 are sufficiently similar, the devices 102 and 104 may be associated with one another.

In some implementations comparison of actuation times may involve comparison of a first indication representative of a time (or times) of actuation of a user input device of one device (e.g., device 102) with a second indication representative of a time (or times) of actuation of a user input device of another device (e.g., device 104). For example, the association processor 122 may acquire the first indication via a user input device of device 102 and receive the second indication from the device 104. The association processor 122 may then compare the two indications to determine whether the actuation of the user input device of the device 102 occurred substantially simultaneously with the actuation of the user input device of the device 104.

Although block 212 follows block 210 in the example of FIG. 2, these operations are not necessarily performed in the illustrated order. For example, in some implementations the synchronization test may be performed before the commencement of an association procedure (e.g., as a prerequisite to commencing the association procedure). In addition, in some implementations a synchronization test may serve as both a prerequisite to an association procedure and form a part of an association procedure.

As represented by block 214, in some implementations the association procedure may involve authenticating the devices 102 and 104 with respect to one another. In general, authentication relates to verifying an identity of another device. Through the use of an authentication procedure, a device may verify that is authorized to communicate with the other device and verify that a given set of operations may be performed in conjunction with the other device. As an example of the latter scenario, a given device may allow a requesting device to access certain services provided by the device if the requesting device has appropriate authorization. Such services may include, for example, connection to a network, access to a pay-per-view service, access to protected media such as data, audio, video, or some combination thereof Authentication may be performed in a variety of ways. In some implementations an authentication procedure may involve sending security credentials (e.g., passwords) and/or user biometric information from one device to another. In a typical scenario, each device will authenticate the other device. For example, the device 102 may authenticate the device 104 and the device 104 may authenticate the device 102. Thus, as represented by block 310 of FIG. 3, the device 104 may perform operations that are similar and/or complementary to the operations of block 214. In this way, each device may send security credentials or other suitable information to the other device and receive corresponding information from the other device.

In view of the above, it should be appreciated that association-related operations may be invoked, terminated, or affected by any suitable distance-related characteristics of two or more devices. For example, association operations may depend on an absolute distance between devices, a defined pattern of distances between devices, a rate of change in relative distance between devices, a relative acceleration between devices, or some combination thereof. Thus, association may depend (e.g., is invoked, terminated, affected, etc.) on whether a measured parameter (e.g., distance, rate of change, or acceleration) between devices is less than, greater than, or substantially similar to (e.g., equal to) a threshold value (e.g., a corresponding defined parameter), or is below, above, or within a range of such threshold values.

Consequently, a diverse range of association functionality may be provided in accordance with teachings herein. For example, an association procedure may be initiated once an incoming device is close enough to an existing device. Such an approach may prove advantageous in the event the surrounding area includes a large number of devices associated with various networks.

In some aspects a user may press a button to activate association and may then use the motion of physically bringing a first device close to and then away from the second device to associate the two devices. This approach allows for an intuitive association method that may also provide a mechanism for readily differentiating the associating devices from other wireless devices in the same area.

In addition, if a user is using a device to wirelessly send a password to a computer, then the computer could "select" the correct device in the immediate vicinity based on which device is currently stationary, in addition to other factors such as distance. Similarly if the user walks up to a computer the computer may turn on or configure itself in an appropriate manner. Further, if multiple users are near the computer, the computer may configure itself based on the closest user, or based on the closest user with the highest priority. In contrast, if the user walks past the computer, the computer may more quickly go back to sleep.

The use of distance-based techniques as taught herein may be employed in conjunction with a variety of association-related operations (e.g., pairing, authentication, etc.). For example, a point-of-sale terminal may utilize a distance parameter and/or a rate of change in relative distance parameter to identify a device to be used for a sales transaction. Here, a rate of change in relative distance may be used to measure a swiping action at the point-of-sale as a user moves one device (e.g., a point-of-sale enabled cell phone) across a second device (the point-of-sale terminal) to initiate a transaction. This technique may provide an effective way to differentiate between other devices in the surrounding area, and may provide a relatively simple user interface for the transaction.

Association may be one-to-one, one-to-many, many-to-one, or many-to-many. For example, an audio device (e.g., an MP3 player) may associate with several nearby headsets to enable the users of those headsets to listen to the audio provided by the audio device. It should be appreciated that the above examples are merely illustrative of a few applications and that distance-based association may be employed in a wide variety of applications.

As represented by block 216, presence management may be provided based on one or more distances between devices. In some aspects this form of presence management relates to the performance of certain operations based on a location of a device with respect to another device and/or motion of the device with respect to the other device. In some aspects presence management also may be based on an identity of a device (e.g., the other device). For example, certain actions may be taken for certain devices. Here a device may be identified by a unique address, an assigned identifier, or in some other manner.

Presence management operations may, in some aspects, relate to invoking presence management, determining whether certain operations are to be performed in conjunction with presence management, and terminating presence management. For example, a computer may present different user interfaces depending upon which user is sitting in front of the computer. To this end, the user may possess a device that enables the computer to uniquely identify the user. Similarly, a presence management-enabled device may be adapted to modify the characteristics of a room (e.g., the lighting, the temperature, music being played, etc.) based on which person or persons are in the room. In another example, the user interface of a portable device (e.g., a cell phone) may be adapted to provide remote control functionality when the portable device is close to a stereo, a television, or some other device that may be controlled. These are but a few examples of presence management. It should be understood that presence management encompasses many other scenarios and operations.

In some implementations, presence management functionality may be employed independently of the association-related functionality discussed above. For example, distance-based presence management as taught herein may be employed in a device that utilizes an association procedure or in a device that does not utilize an association procedure. In the former case, distance-based presence management as taught herein may be employed in a device where the association is not distance-based. Also, a device employing distance-based association as taught herein may or may not provide presence management functionality.

Referring to the example of FIG. 2, operations similar to the operations of blocks 202, 204, 206, 208, and 212 may be performed in conjunction with presence management. For example, a decision as to whether to invoke or terminate presence management may be based on the result of (e.g., the indication generated from) the comparison operations of block 208 and/or the synchronization operations of block 212. Thus, presence management may be automatically invoked if the devices are within a given distance of one another (e.g., 3 meters) and/or are moved in a certain manner with respect to one another. Similarly, one or more of the operations performed during presence management may be based on the results of the comparison of block 208.

In a similar manner as discussed above for association, although block 216 follows blocks 204 through 208 in the example of FIG. 2, these operations are not necessarily performed in the illustrated order. For example, in some implementations the distance determining operations may be performed after the commencement of a presence management procedure. Thus, one or more distance-related functions as taught herein may be invoked as part of a presence management procedure. In addition, in some implementations distance determining operations may serve as both a prerequisite to a presence management procedure and form a part of a presence management procedure.

Presence management may involve operations performed by the device 102 as well as, in some circumstances, operations performed by the device 104. Accordingly, as represented by block 312 of FIG. 3, the device 104 may perform operations that are similar and/or complementary to the operations of blocks 216.

In some aspects a device (e.g., the device 102, the device 104, or both) may be configured based on a distance-related indication. Such configuration may include, in some aspects, one or more of configuring an output of a user interface, invoking a function, adapting operations, and providing access to functionality. In some aspects the configuration may be based on the identity of another device. For example, the device 102 may be configured based on the identity of the device 104, or vice versa. In some aspects a device may transmit information to or receive information from another device, wherein the information is based on the indication. As an example, such information may be generated, selected, or modified depending upon the indication.

In a typical implementation presence management may be employed in the device 102 to affect the operation of the device 102 if the device 102 is brought within a specified range of device 104 and/or is moved in an appropriate manner with respect to device 104. In one sample use case presence management may configure the device 102 to provide remote control functionality capable of controlling the device 104. In conjunction with this reconfiguration, the device 102 may present a different interface to the user by, for example, modifying a display of the display screen and modifying the functionality of one or more input devices (e.g., buttons or soft keys) of the device 102. In addition, the device 102 may be enabled to send uniquely configured information (e.g., remote control instructions, etc.) to the device 104.

As a device 102 is brought within a specified range of device 104 and/or is moved in an appropriate manner with respect to the device 104, presence management also may be employed in the device 104 to affect its operation. Continuing with the sample use case mentioned above, the device 104 may now enable the device 102 (e.g., and no other devices) to control selected functionality of the device 104 or of one or more other devices if distance-based conditions, and optionally device identity conditions, are met. For example, the device 104 may present a unique interface to the user of device 102 by modifying the display on the display screen of the device 104 or another device (e.g., a television or a television receiver). In some aspects the device 104 may provide presence management for the device 102 based on the indication by, for example, facilitating configuration of the device 102. To this end, the device 104 may send appropriate messages to the device 102 that facilitate configuration of the device 102 (e.g., as discussed above). In a typical example, configuration of the device 102 may include modifying the output of the user interface of the device 102.

In another sample use case, a given device such as device 104 may allow access to certain of its functionality depending on the identity of another device and depending on at least one distance between the devices. In the example of FIG. 1, if the identity and distance-based conditions are met, the device 104 may provide uniquely configured information to the device 102. For example, the presence management functionality enabled on the device 104 may provide access to a service such as network connectivity or pay-for-use media such as data, audio, and video. It should be appreciated that the presence management functionality enabled on the device 104 may take various other forms Presence management operations may be invoked, terminated, or affected by any suitable distance-related characteristics of two or more devices. For example, presence management operations may depend on an absolute distance between devices, a defined pattern of distances between devices, a rate of change in relative distance between devices, a relative acceleration between devices, or some combination thereof. Thus, presence management may depend (e.g., is invoked, terminated, affected, etc.) on whether a measured parameter (e.g., distance, rate of change, or acceleration) between devices is less than, greater than, or substantially similar to (e.g., equal to) a threshold value (e.g., a corresponding defined parameter), or is below, above, or within a range of such threshold values.

Consequently, a diverse range of presence management functionality may be provided in accordance with teachings herein. For example, if a user runs into a room with a presence-management enabled device then sits on the couch, a presence-management-enabled television may turn on to breaking news. Conversely, if the same user walks into the room and sits on the couch, the television may turn on and play a recent recording of the user's favorite program.

Figure 5:
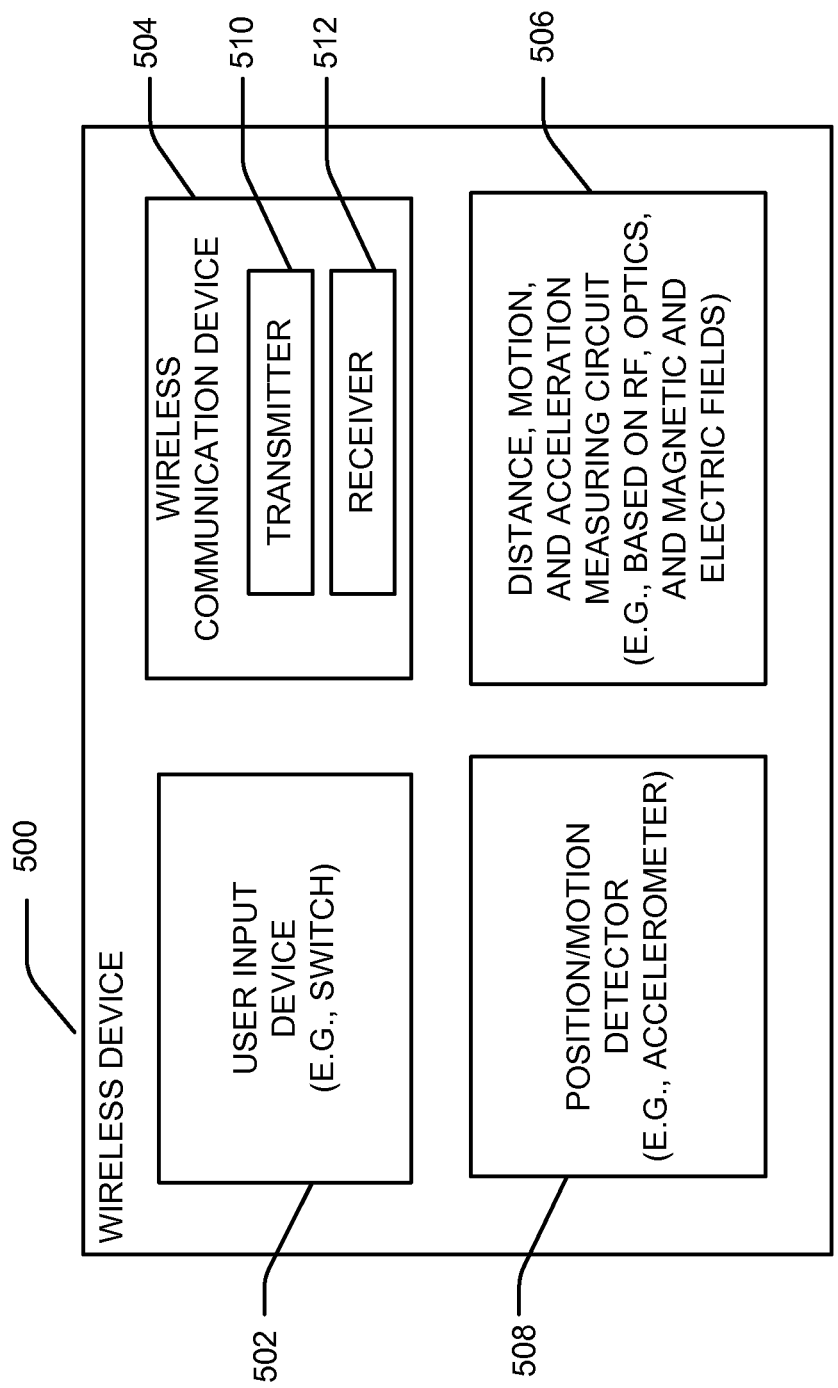
FIG. 5 is a simplified block diagram of several sample aspects of a wireless device adapted to perform distance-based operations.

It should be appreciated that the components described herein may take a variety of forms. For example, FIG. 5 illustrates that a wireless device 500 (e.g., similar to the device 102 and/or the device 104) may include in broad terms functionality relating to a user input device 502, a communication device 504, a distance, motion, and acceleration measuring circuit 506, and a position/motion detector 508.

The user input device 502 may comprise one or more of a variety of components that enable a user to provide some form of input to the wireless device 500. For example, the user input device 502 may comprise one or more switches such as a pushbutton or a keypad. The user input device 502 also may comprise a touch-screen, a touchpad, or other similar input mechanism. The user input device 502 may comprise a pointing device such as a mouse, trackball, an electronic pen, a pointing stick, etc. The user input device 502 also may be adapted to receive non-mechanical forms of input such as an audio (e.g., voice) input, an optical-based input, an RF-based input, or some other suitable form of input. As discussed above, the user input device 502 may be utilized by the user to initiate some function in the wireless device such as facilitating authentication or presence management. As an example of the latter case, the user input device 502 may comprise the input device discussed above that is activated at substantially the same time on both of the devices 102 and 104.

The communication device 504 may comprise various components that facilitate communicating with another device. For example, as discussed herein the communication device 504 may comprise a radio (e.g., the radio 110 and/or the radio 126) with associated transmitter and receiver components 510 and 512, respectively, that include various components (e.g., signal generators and signal processors) that facilitate communication over a wireless medium.

The communication device 504 may employ a variety of wireless physical layer schemes. For example, the physical layer may utilize some form of CDMA, TDMA, OFDM, OFDMA, or other modulation and multiplexing schemes.

In some aspects the communication device 504 may communicate via a pulsed-based physical layer. In some aspects the physical layer may utilize ultra-wideband pulses that have a relatively short length (e.g., on the order of a few nanoseconds) and a relatively wide bandwidth. In some aspects an ultra-wide band system may be defined as a system having a fractional bandwidth on the order of approximately 20% or more and/or having a bandwidth on the order of approximately 500 MHz or more.

The circuit 506 may comprise one or more of a variety of components adapted to measure one or more of distance, motion, and acceleration. As discussed above, various techniques may be employed to measure distance including, for example, two-way ranging, interrogations/response signals, received power measurements, acceleration readings, digital or analog imaging, detecting changes in electrical and magnetic fields, and detecting a Doppler shift in signals. Accordingly, the circuit 506 may employ corresponding circuitry (e.g., RF circuitry, optics, accelerometers, signal strength sensors, electrical and magnetic fields sensors, or Doppler shift sensors) to measure distance using one or more these techniques. In a specific example, an optical device such as a video device may employ video processing to compute the rate of change in relative distance based on frame differences and similarities. In another example, the rate of change in relative distance may be determined by identifying a rate of change in the relative orientation of electrical and magnetic fields. Also, in some applications an accelerometer may be used to obtain a measurement of distance, velocity, or acceleration.

In some implementations, one or more of the components of the circuit 506 may be implemented in the wireless communication device 504. For example, an implementation that determines distance by calculating the round-trip time of RF signals may utilize the transmitter and receiver components of a radio to transmit and receive ranging signals (e.g., ultra-wideband pulses) or other signals that are used to calculate a round-trip time.

In some implementations a position and/or motion detector 508 may be employed to determine one or more distance-related parameters associated with two or more devices. For example, through the use of an accelerometer in one or more of the devices, the rate of change in relative distance between two devices may be more easily obtained or determined with greater accuracy. In some implementations one or more of the components the position/motion detector 508 may be implemented in the circuit 506.

The teachings herein may be incorporated into (e.g., implemented within or performed by) a variety of devices. For example, one or more aspects taught herein may be incorporated into a phone (e.g., a cellular phone), a personal data assistant ("PDA"), an entertainment device (e.g., a music or video device), a headset (e.g., headphones, an earpiece, etc.), a microphone, a medical device (e.g., a biometric sensor, a heart rate monitor, a pedometer, an EKG device, etc.), a user I/O device (e.g., a watch, a remote control, a light switch, a keyboard, a mouse, etc.), a tire pressure monitor, a computer, a point-of-sale device, an entertainment device, a hearing aid, a set-top box, or any other suitable device. Moreover, these devices may have different power and data requirements. In some aspects, the teachings herein may be adapted for use in low power applications (e.g., through the use of a pulse-based signaling scheme and low duty cycle modes) and may support a variety of data rates including relatively high data rates (e.g., through the use of high-bandwidth pulses).

Figure 6:
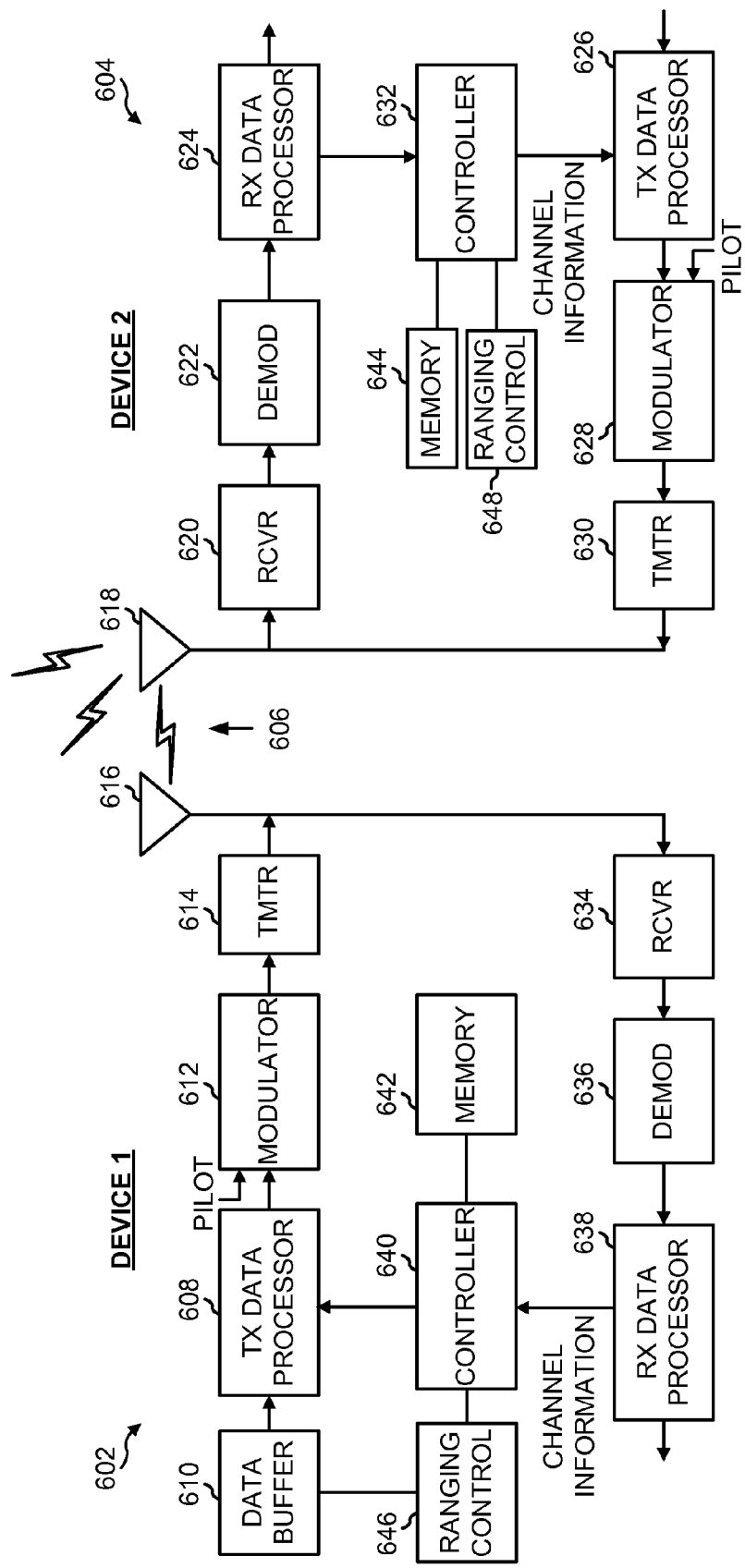
FIG. 6 is a simplified block diagram of several sample aspects of communication components.

The teachings herein may be incorporated into a device employing various components for communicating with at least one other device. FIG. 6 depicts several sample components that may be employed to facilitate communication between devices. Here, a first device (e.g., an access terminal) 602 and a second device (e.g., an access point) 604 are adapted to communicate via a communication link 606 over a suitable medium.

Initially, components involved in sending information from the device 602 to the device 604 (e.g., a reverse link) will be treated. A transmit ("TX") data processor 608 receives traffic data (e.g., data packets) from a data buffer 610 or some other suitable component. The transmit data processor 608 processes (e.g., encodes, interleaves, and symbol maps) each data packet based on a selected coding and modulation scheme, and provides data symbols. In general, a data symbol is a modulation symbol for data, and a pilot symbol is a modulation symbol for a pilot (which is known a priori). A modulator 612 receives the data symbols, pilot symbols, and possibly signaling for the reverse link, and performs modulation (e.g., OFDM or some other suitable modulation) and/or other processing as specified by the system, and provides a stream of output chips. A transmitter ("TMTR") 614 processes (e.g., converts to analog, filters, amplifies, and frequency upconverts) the output chip stream and generates a modulated signal, which is then transmitted from an antenna 616.

The modulated signals transmitted by the device 602 (along with signals from other devices in communication with the device 604) are received by an antenna 618 of the device 604. A receiver ("RCVR") 620 processes (e.g., conditions and digitizes) the received signal from the antenna 618 and provides received samples. A demodulator ("DEMOD") 622 processes (e.g., demodulates and detects) the received samples and provides detected data symbols, which may be a noisy estimate of the data symbols transmitted to the device 604 by the other device(s). A receive ("RX") data processor 624 processes (e.g., symbol demaps, deinterleaves, and decodes) the detected data symbols and provides decoded data associated with each transmitting device (e.g., device 602).

Components involved in sending information from the device 604 to the device 602 (e.g., a forward link) will be now be treated. At the device 604, traffic data is processed by a transmit ("TX") data processor 626 to generate data symbols. A modulator 628 receives the data symbols, pilot symbols, and signaling for the forward link, performs modulation (e.g., OFDM or some other suitable modulation) and/or other pertinent processing, and provides an output chip stream, which is further conditioned by a transmitter ("TMTR") 630 and transmitted from the antenna 618. In some implementations signaling for the forward link may include power control commands and other information (e.g., relating to a communication channel) generated by a controller 632 for all devices (e.g. terminals) transmitting on the reverse link to the device 604.

At the device 602, the modulated signal transmitted by the device 604 is received by the antenna 616, conditioned and digitized by a receiver ("RCVR") 634, and processed by a demodulator ("DEMOD") 636 to obtain detected data symbols. A receive ("RX") data processor 638 processes the detected data symbols and provides decoded data for the device 602 and the forward link signaling. A controller 640 receives power control commands and other information to control data transmission and to control transmit power on the reverse link to the device 604.

The controllers 640 and 632 direct various operations of the device 602 and the device 604, respectively. For example, a controller may determine an appropriate filter, reporting information about the filter, and decode information using a filter. Data memories 642 and 644 may store program codes and data used by the controllers 640 and 632, respectively.

FIG. 6 also illustrates that the communication components may include one or more components that perform ranging-related operations as taught herein. For example, a ranging control component 646 may cooperate with the controller 640 and/or other components of the device 602 to send and receive ranging-related signals and information to another device (e.g., device 604). Similarly, a ranging control component 648 may cooperate with the controller 632 and/or other components of the device 604 to send and receive ranging-related signals and information to another device (e.g., device 602).

Figure 7:
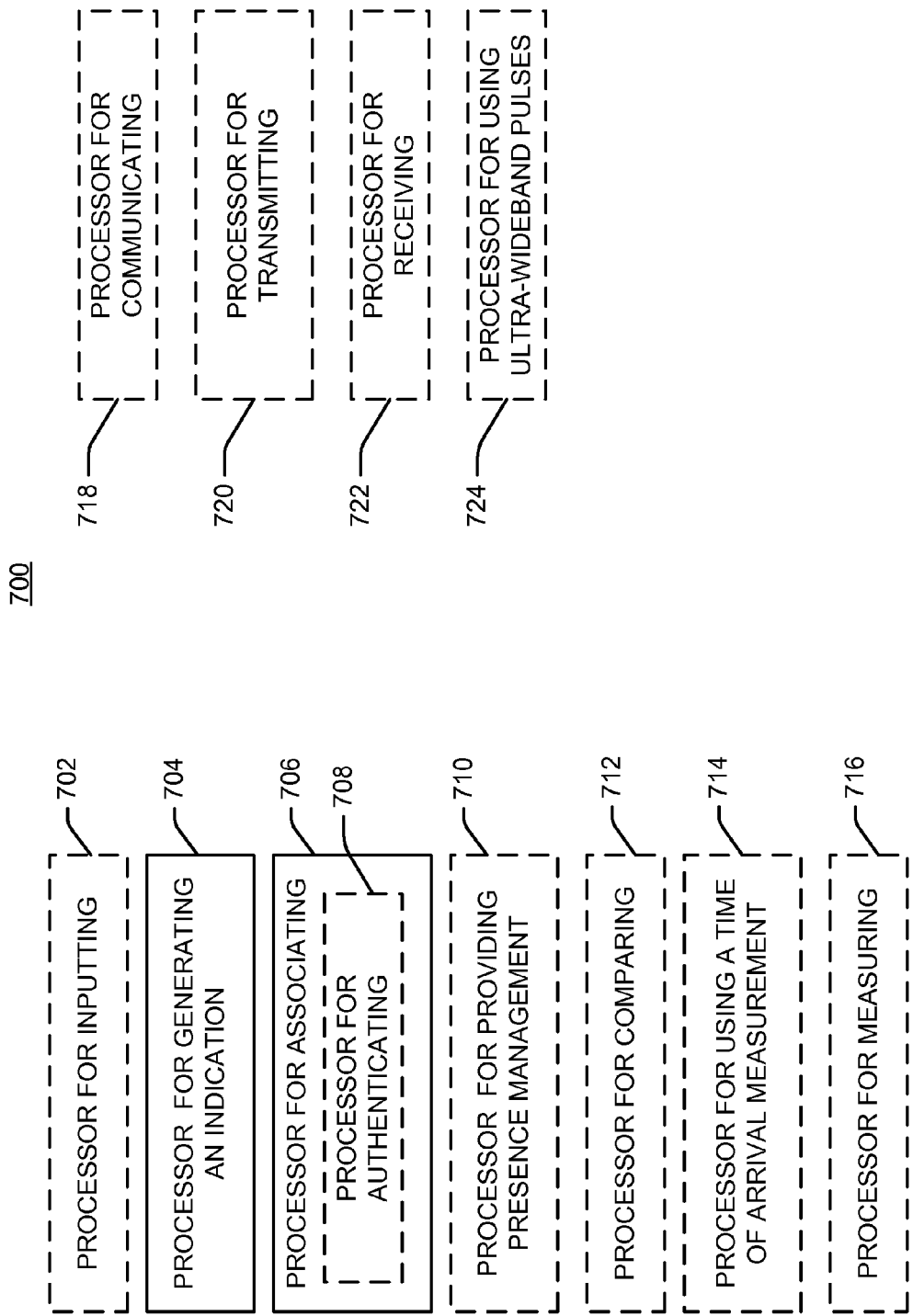
FIG. 7 is a simplified block diagram of several sample aspects of a device adapted to perform distance-based operations.

The components described herein may be implemented in a variety of ways. Referring to FIG. 7, an apparatus 700 is represented as a series of interrelated functional blocks that may represent functions implemented by, for example a processor, software, some combination thereof, or in some other manner as taught herein.

As shown in FIG. 7, the apparatus 700 may include one or more modules 702, 704, 706, 708, 710, 712, 714, 716, 718, 720, 722, and 724 that may perform one or more of the functions described above with regard to various figures. For example, a processor for inputting 702 may facilitate user input and may correspond to, for example, component 502 discussed above. A processor for generating an indication 704 may generate one or more indications as taught herein and may correspond to, for example, component 112 and/or component 138 discussed above. A processor for associating 706 may provide various functionality relating to association as taught herein and may correspond to, for example, component 120 and/or component 130 discussed above. A processor for authenticating 708 may provide various functionality relating to authentication as taught herein and may correspond to, for example, component 122 and/or component 132 discussed above. A processor for providing presence management 710 may provide various functionality relating to presence management as taught herein and may correspond to, for example, component 124 and/or component 134 discussed above. A processor for comparing 712 may provide various functionality relating to comparing distance-based information as taught herein and may correspond to, for example, component 114 discussed above. A processor for using a time-of-arrival measurement 714 may provide various functionality relating to time-of-arrival measurements as taught herein and may correspond to, for example, component 108 and/or component 136 discussed above. A processor for measuring 716 may provide various functionality relating to measuring distance as taught herein and may correspond to, for example, component 108 and/or component 136 discussed above. A processor for communicating 718 may provide various functionality relating to communicating with another device as taught herein and may correspond to, for example, component 504 discussed above. A processor for transmitting 720 may provide various functionality relating to transmitting information to another device as taught herein and may correspond to, for example, component 510 discussed above. A processor for receiving 722 may provide various functionality relating to receiving information from another device as taught herein and may correspond to, for example, component 512 discussed above. A processor for using ultra-wideband pulses may provide various functionality relating to determining distance using ultra-wideband pulses as taught herein and may correspond to, for example, component 108 and/or component 110 discussed above.

As noted above, FIG. 7 illustrates that in some aspects these components may be implemented via appropriate processor components. These processor components may in some aspects be implemented, at least in part, using structure as taught herein. In some aspects a processor may be adapted to implement a portion or all of the functionality of one or more of these components. In some aspects one or more of the components represented by dashed boxes are optional.

In some aspects the apparatus 700 may comprise an integrated circuit. Thus, the integrated circuit may comprise one or more processors that provide the functionality of the processor components illustrated in FIG. 7. For example, in some aspects a single processor may implement the functionality of the illustrated processor components, while in other aspects more than one processor may implement the functionality of the illustrated processor components. In addition, in some aspects the integrated circuit may comprise other types of components that implement some or all of the functionality of the illustrated processor components.

In addition, the components and functions represented by FIG. 7, as well as other components and functions described herein, may be implemented using any suitable means. Such means also may be implemented, at least in part, using corresponding structure as taught herein. For example, in some aspects means for inputting may comprise a user input device, means for generating an indication may comprise an indication generator, means for associating may comprise an association processor, means for authenticating may comprise an authentication processor, means for providing presence management may comprise a presence management processor, means for comparing may comprise a comparator, means for using a time-of-arrival measurement may comprise a distance determiner, means for measuring may comprise a distance determiner, means for communicating may comprise a radio, means for transmitting may comprise a transmitter, means for receiving may comprise a receiver, and means for using ultra-wideband pulses may comprise a radio. One or more of such means also may be implemented in accordance with one or more of the processor components of FIG. 7.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that any of the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the aspects disclosed herein may be implemented within or performed by an integrated circuit ("IC"), an access terminal, or an access point. The IC may comprise a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

The steps of a method or algorithm described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such the processor can read information (e.g., code) from and write information to the storage medium. A sample storage medium may be integral to the processor. The processor and the storage medium may reside in an ASIC. The ASIC may reside in user equipment. In the alternative, the processor and the storage medium may reside as discrete components in user equipment. Moreover, in some aspects any suitable computer-program product may comprise a computer-readable medium comprising codes (e.g., executable by at least one computer) relating to one or more of the aspects of the disclosure. In some aspects a computer program product may comprise packaging materials.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the scope of the disclosure. Thus, the present disclosure is not intended to be limited to the aspects shown herein but is to be accorded the widest scope consistent with the principles and novel features disclosed herein.

What is claimed is:

1. A method of performing an operation based on distance, comprising:
   receiving, at a first device, a plurality of distinct signals from a second device and one or more other devices, respectively;
   generating, at the first device, a plurality of indications related to a plurality of distinct distances between the first device and the second device and the one or more other devices based on the plurality of distinct signals, wherein the first device communicates with the second device and the one or more other devices via one or more wireless communication links;
   associating the first device with the second device based on the plurality of indications and a criteria based on the distance between the first device and second device relative to the one or more distances between the first device and the one or more other devices, wherein associating the first device and the second device comprises:
      instructing a user to actuate a first switch of the first device;
      acquiring a first indication representative of a time of actuation of the first switch of the first device;
      receiving a second indication representative of a time of actuation of a second switch of the second device; and
      comparing the first indication with the second indication to determine whether the actuation of the first switch of the first device occurred substantially simultaneously with the actuation of the second switch of the second device; and
   transmitting an association related signal to the second device.

2. The method of claim 1, further comprising associating the first device with a third device.

3. The method of claim 1, wherein the association comprises authenticating the first device with the second device.

4. The method of claim 3, wherein the authentication comprises transmitting at least one security credential or biometric information to the second device.

5. The method of claim 3, wherein the authentication comprises receiving at least one security credential or biometric information from the second device.

6. The method of claim 1, further comprising providing presence management for the first device.

7. The method of claim 6, wherein providing the presence management further comprises configuring the first device based on the indication related to the distance between the first and second devices.

8. The method of claim 6, wherein providing the presence management comprises receiving, from the second device, information that is based on an identity of the first device.

9. The method of claim 1, further comprising providing presence management for the second device.

10. The method of claim 9, wherein providing the presence management for the second device comprises configuring at least one device based on an identity of the second device.

11. The method of claim 9, wherein providing the presence management for the second device comprises providing, to the second device, information that is based on an identity of the second device.

12. The method of claim 1, wherein the association comprises establishing application-level communication with the second device.

13. The method of claim 1, further comprising comparing, at the first device, the indication related to the distance between the first and second devices with a threshold, wherein the association is performed if the indication is less than or equal to the threshold.

14. The method of claim 1, wherein the indication related to the distance between the first and second devices comprises a rate of change in distance between the first device and the second device.

15. The method of claim 14, further comprising comparing the rate of change in distance with a defined rate of change, wherein the association is performed if a result of the comparison meets a second criteria, wherein the second criteria comprises at least one of the group consisting of:
   the rate of change in distance is less than the defined rate of change;
   the rate of change in distance is greater than the defined rate of change;
   the rate of change in distance is equal to the defined rate of change; and
   the rate of change in distance is substantially equal to the defined rate of change.

16. The method of claim 1, wherein the indication related to the distance between the first and second devices comprises an acceleration profile between the first device and the second device.

17. The method of claim 16, further comprising comparing the acceleration profile with a defined acceleration profile, wherein the association is performed if the acceleration profile is substantially similar to the defined acceleration profile.

18. The method of claim 1, wherein the indication related to the distance between the first and second devices comprises a pattern of distances between the first device and the second device.

19. The method of claim 18, further comprising comparing the pattern of distances with a defined pattern, wherein the association is performed if the pattern of distances is substantially similar to the defined pattern.

20. The method of claim 1, further comprising automatically commencing the generation of the indications related to the plurality of the distinct distances.

21. The method of claim 1, further comprising commencing the generation of the indications related to the plurality of the distinct distances in response to a request from a user.

22. The method of claim 1, further comprising using a time-of arrival measurement scheme to determine the indications related to the plurality of the distinct distances.

23. The method of claim 1, further comprising measuring at least one round-trip time to determine the indications related to the plurality of the distinct distances.

24. The method of claim 1, further comprising measuring signal strength of the plurality of distinct signals to determine the indications related to the plurality of the distinct distances.

25. The method of claim 1, further comprising receiving information from the second device to generate at least one of the indications related to the plurality of the distinct distances.

26. The method of claim 1, further comprising using ultra-wideband pulses to determine the indications related to the plurality of the distinct distances.

27. The method of claim 26, wherein the ultra-wideband pulses have a fractional bandwidth on the order of 20% or more, have a bandwidth on the order of 500 MHz or more, or have a fractional bandwidth on the order of 20% or more and have a bandwidth on the order of 500 MHz or more.

28. The method of claim 1, wherein the first device communicates with the second device via a personal area network or a body area network.

29. An apparatus for performing an operation based on distance, comprising:
    a user interface device;
    a first switch;
    a receiver adapted to receive a plurality of distinct signals from a device and one or more other devices, respectively;
    a distance measuring generator adapted to generate a plurality of indications related to a plurality of distinct distances between the apparatus and the device and the one or more other devices based on the plurality of distinct signals, wherein the apparatus communicates with the device and the one or more other devices via one or more wireless communication links;
    an association processor adapted to associate the apparatus with the device based on the plurality of indications and a criteria based on the distance between the apparatus and the device relative to the one or more distances between the apparatus and the one or more other devices, wherein the association processor is further adapted to:
        provide an instruction to actuate the first switch to a user via the user interface device;
        acquire a first indication representative of a time of actuation of the first switch of the apparatus;
        receive a second indication representative of a time of actuation of a second switch of the device; and
        compare the first indication with the second indication to determine whether the actuation of the first switch of the apparatus occurred substantially simultaneously with the actuation of the second switch of the device; and
    a transmitter adapted to transmit an association related signal to the device in response to a command generated by the association processor.

30. The apparatus of claim 29, wherein the association processor is further adapted to associate the apparatus with a third device.

31. The apparatus of claim 29, wherein the association processor further comprises an authentication processor adapted to authenticate the apparatus with the device.

32. The apparatus of claim 31, wherein the authentication processor is further adapted to cooperate with the transmitter to transmit at least one security credential or biometric information to the device.

33. The apparatus of claim 31, wherein the authentication processor is further adapted to cooperate with the receiver to receive at least one security credential or biometric information from the device.

34. The apparatus of claim 29, further comprising a presence management processor adapted to provide presence management for the apparatus.

35. The apparatus of claim 34, wherein the presence management processor is further adapted to configure the apparatus based on the indication related to the distance between the apparatus and the device.

36. The apparatus of claim 34, wherein the presence management processor is further adapted to cooperate with the receiver to receive, from the device, information that is based on an identity of the apparatus.

37. The apparatus of claim 29, wherein the presence management processor is further adapted to provide presence management for the device.

38. The apparatus of claim 37, wherein the presence management processor is further adapted to configure at least one device based on an identity of the device.

39. The apparatus of claim 37, wherein the presence management processor is further adapted to provide, to the device, information that is based on an identity of the device.

40. The apparatus of claim 29, wherein the association processor is further adapted to establish application-level communication with the device.

41. The apparatus of claim 29, further comprising a comparator adapted to compare the indication related to the distance between the apparatus and the device with a threshold, wherein the association processor is further adapted to perform the association if the indication is less than or equal to the threshold.

42. The apparatus of claim 29, wherein the indication related to the distance between the apparatus and the device comprises a rate of change in distance between the apparatus and the device.

43. The apparatus of claim 42, further comprising a comparator adapted to compare the rate of change in distance with a defined rate of change, wherein the association processor is further adapted to perform the association if a result of the comparison meets a second criteria, wherein the second criteria comprises at least one of the group consisting of:
    the rate of change in distance is less than the defined rate of change;
    the rate of change in distance is greater than the defined rate of change;
    the rate of change in distance is equal to the defined rate of change; and
    the rate of change in distance is substantially equal to the defined rate of change.

44. The apparatus of claim 29, wherein the indication related to the distance between the apparatus and the device comprises an acceleration profile between the apparatus and the device.

45. The apparatus of claim 44, further comprising a comparator adapted to compare the acceleration profile with a defined acceleration profile, wherein the association processor is further adapted to perform the association if the acceleration profile is substantially similar to the defined acceleration profile.

46. The apparatus of claim 29, wherein the indication related to the distance between the apparatus and the device comprises a pattern of distances between the apparatus and the device.

47. The apparatus of claim 46, further comprising a comparator adapted to compare the pattern of distances with a defined pattern, wherein the association processor is further adapted to perform the association if the pattern of distances is substantially similar to the defined pattern.

48. The apparatus of claim 29, wherein the distance measuring generator is further adapted to automatically commence the generation of the indications related to the plurality of distinct distances.

49. The apparatus of claim 29, wherein the distance measuring generator is further adapted to commence the generation of the indications related to the plurality of distinct distances in response to a request from a user.

50. The apparatus of claim 29, wherein the distance measuring generator is adapted to use a time-of-arrival measurement scheme to determine the indications related to the plurality of distinct distances.

51. The apparatus of claim 29, wherein the distance measuring generator is adapted to measure at least one round-trip time to determine the indications related to the plurality of distinct distances.

52. The apparatus of claim 29, wherein the distance measuring generator is adapted to measure signal strength of the plurality of distinct signals to determine the indications related to the plurality of distinct distances.

53. The apparatus of claim 29, wherein the receiver is adapted to receive information from the device, wherein the distance measuring generator uses the received information to generate at least one of the indications related to the plurality of distinct distances.

54. The apparatus of claim 29, further comprising a radio adapted to use ultra-wideband pulses to determine the indications related to the plurality of distinct distances.

55. The apparatus of claim 54, wherein the ultra-wideband pulses have a fractional bandwidth on the order of 20% or more, have a bandwidth on the order of 500 MHz or more, or have a fractional bandwidth on the order of 20% or more and have a bandwidth on the order of 500 MHz or more.

56. The apparatus of claim 29, wherein the apparatus communicates with the device via a personal area network or a body area network.

57. An apparatus for performing an operation based on distance, comprising:
means for interfacing with a user;
first switching means;
means for receiving a plurality of distinct signals from a device and one or more other devices, respectively;
means for generating a plurality of indications related to a plurality of distinct distances between the apparatus and the device and the one or more other devices based on the plurality of distinct signals, wherein the apparatus communicates with the device and the one or more other devices via one or more wireless communication links;
means for associating the apparatus with the device based on the plurality of indications and a criteria based on the distance between the apparatus and the device relative to the one or more distances between the apparatus and the one or more other devices, wherein the means for associating is configured to:
provide instruction to actuate the first switching means to a user by way of the user interfacing means;
acquire a first indication representative of a time of actuation of the first switching means of the apparatus;
receive a second indication representative of a time of actuation of a second switching means of the device; and
compare the first indication with the second indication to determine whether the actuation of the first switching means of the apparatus occurred substantially simultaneously with the actuation of the second switching means of the device; and means for transmitting an association related signal to the device.

58. The apparatus of claim 57, wherein the means for associating associates the apparatus with a third device.

59. The apparatus of claim 57, wherein the means for associating comprises means for authenticating the apparatus with the device.

60. The apparatus of claim 59, wherein the means for authenticating cooperates with the means for transmitting to transmit at least one security credential or biometric information to the device.

61. The apparatus of claim 59, wherein the means for authenticating cooperates with the means for receiving to receive at least one security credential or biometric information from the device.

62. The apparatus of claim 57, further comprising means for providing presence management for the apparatus.

63. The apparatus of claim 62, wherein the means for providing presence management configures the apparatus based on the indication related to the distance between the apparatus and the device.

64. The apparatus of claim 62, wherein the means for providing presence management cooperates with the means for receiving to receive, from the device, information that is based on an identity of the apparatus.

65. The apparatus of claim 57, further comprising means for providing presence management for the device.

66. The apparatus of claim 65, wherein the means for providing presence management for the device configures at least one device based on an identity of the device.

67. The apparatus of claim 65, wherein the means for providing presence management for the device provides, to the device, information that is based on an identity of the device.

68. The apparatus of claim 57, wherein the means for associating establishes application-level communication with the device.

69. The apparatus of claim 57, further comprising means for comparing the indication related to the distance between the apparatus and the device with a threshold, wherein the means for associating performs the association if the indication is less than or equal to the threshold.

70. The apparatus of claim 57, wherein the indication related to the distance between the apparatus and the device comprises a rate of change in distance between the apparatus and the device.

71. The apparatus of claim 70, further comprising means for comparing the rate of change in distance with a defined rate of change, wherein the means for associating performs the association if a result of the comparison meets a second criteria, wherein the second criteria comprises at least one of the group consisting of:
the rate of change in distance is less than the defined rate of change;
the rate of change in distance is greater than the defined rate of change;
the rate of change in distance is equal to the defined rate of change; and
the rate of change in distance is substantially equal to the defined rate of change.

72. The apparatus of claim 57, wherein the indication related to the distance between the first and second devices comprises an acceleration profile between the apparatus and the device.

73. The apparatus of claim 72, further comprising means for comparing the acceleration profile with a defined acceleration profile, wherein the means for associating performs the association if the acceleration profile is substantially similar to the defined acceleration profile.

74. The apparatus of claim 57, wherein the indication related to the distance between the first and second devices comprises a pattern of distances between the apparatus and the device.

75. The apparatus of claim 74, further comprising means for comparing the pattern of distances with a defined pattern, wherein the means for associating performs the association if the pattern of distances is substantially similar to the defined pattern.

76. The apparatus of claim 57, wherein the means for generating the indications related to the plurality of distinct distances automatically commences the generation of the at least one determined distance.

77. The apparatus of claim 57, wherein the means for generating the indications related to the plurality of distinct distances commences the generation of the at least one determined distance in response to a request from a user.

78. The apparatus of claim 57, wherein the generating means comprises means for using a time-of-arrival measurement scheme to determine indications related to the plurality of distinct distances.

79. The apparatus of claim 57, wherein the generating means comprises means for measuring at least one round-trip time to determine the indications related to the plurality of distinct distances.

80. The apparatus of claim 57, wherein the generating means comprises means for measuring signal strength of the plurality of distinct signals to determine the indications related to the plurality of distinct distances.

81. The apparatus of claim 57, wherein the means for receiving is adapted to receive information from the device, wherein the means for generating the indications related to the plurality of distinct distances uses the received information to generate the at least one determined distance.

82. The apparatus of claim 57, further comprising means for using ultra-wideband pulses to determine the indications related to the plurality of distinct distances.

83. The apparatus of claim 82, wherein the ultra-wideband pulses have a fractional bandwidth on the order of 20% or more, have a bandwidth on the order of 500 MHz or more, or have a fractional bandwidth on the order of 20% or more and have a bandwidth on the order of 500 MHz or more.

84. The apparatus of claim 57, further comprising means for communicating with the device via a personal area network or a body area network.

85. A computer-program product for performing an operation based on distance, comprising:
a non-transitory computer-readable medium comprising codes executable by at least one computer to:
receive, at a first device, a plurality of distinct signals from a second device and one or more other devices, respectively;
generate, at the first device, a plurality of indications related to a plurality of distinct distances between the first device and the second device and the one or more other devices based on the plurality of distinct signals, wherein the first device communicates with the second device and the one or more other devices via one or more wireless communication links;
associate the first device with the second device based on the plurality of indications and a criteria based on the distance between the first device and second device relative to the one or more distances between the first device and the one or more other devices, wherein associating the first device and the second device further comprises:
instructing a user to actuate a first switch of the first device;
acquiring a first indication representative of a time of actuation of the first switch of the first device;
receiving a second indication representative of a time of actuation of a second switch of the second device; and
comparing the first indication with the second indication to determine whether the actuation of the first switch of the first device occurred substantially simultaneously with the actuation of the second switch of the second device; and
transmitting an association related signal to the second device.

86. A headset for performing an operation based on distance, comprising:
a user interface device;
a first switch;
a receiver adapted to receive a plurality of distinct signals from a device and one or more other devices, respectively;
a distance measuring generator adapted to generate a plurality of indications related to a plurality of distinct distances between the headset and the device and the one or more other devices based on the plurality of distinct signals, wherein the headset communicates with the device and the one or more other devices via one or more wireless communication links;
an association processor adapted to associate the headset with the device based on the plurality of indications and a criteria based on the distance between the headset and the device relative to the one or more distances between the headset and the one or more other devices, wherein the association processor is further adapted to:
provide an instruction to actuate the first switch to a user via the user interface device;
acquire a first indication representative of a time of actuation of the first switch of the headset;
receive a second indication representative of a time of actuation of a second switch of the device; and
compare the first indication with the second indication to determine whether the actuation of the first switch of the headset occurred substantially simultaneously with the actuation of the second switch of the device;
a transmitter adapted to transmit an association related signal to the device in response to a command generated by the association processor; and
a transducer adapted to provide an audible output based on a signal received from the device via the one or more wireless communication links.

87. A watch for performing an operation based on distance, comprising:
a user interface device;
a first switch;
a receiver adapted to receive a plurality of distinct signals from a device and one or more other devices, respectively;
a distance measuring generator adapted to generate a plurality of indications related to a plurality of distinct distances between the watch and the device and the one or more other devices based on the plurality of distinct signals, wherein the watch communicates with the device and the one or more other devices via one or more wireless communication links;

an association processor adapted to associate the watch with the device based on the plurality of indications and a criteria based on the distance between the watch and the device relative to the one or more distances between the watch and the one or more other devices, wherein the association processor is further adapted to:
provide an instruction to actuate the first switch to a user via the user interface device;
acquire a first indication representative of a time of actuation of the first switch of the watch;
receive a second indication representative of a time of actuation of a second switch of the device; and
compare the first indication with the second indication to determine whether the actuation of the first switch of the watch occurred substantially simultaneously with the actuation of the second switch of the device;
a transmitter adapted to transmit an association related signal to the device in response to a command generated by the association processor; and
a display adapted to provide a visual output based on a signal received from the device via the one or more wireless communication links.

88. A medical device for performing an operation based on distance, comprising:
a user interface device;
a first switch;
a receiver adapted to receive a plurality of distinct signals from a device and one or more other devices, respectively;
a distance measuring generator adapted to generate a plurality of indications related to a plurality of distinct distances between the medical device and the device and the one or more other devices based on the plurality of distinct signals, wherein the medical device communicates with the device and the one or more other devices via one or more wireless communication links;
an association processor adapted to associate the medical device with the device based on the plurality of indications and a criteria based on the distance between the medical device and the device relative to the one or more distances between the medical device and the one or more other devices, wherein the association processor is further adapted to:
provide an instruction to actuate the first switch to a user via the user interface device;
acquire a first indication representative of a time of actuation of the first switch of the medical device;
receive a second indication representative of a time of actuation of a second switch of the device; and
compare the first indication with the second indication to determine whether the actuation of the first switch of the medical device occurred substantially simultaneously with the actuation of the second switch of the device;
a sensor adapted to generate sensed signals to be transmitted to the device via the one or more wireless communication links.

* * * * *